US009770469B2

(12) United States Patent
Dekel et al.

(10) Patent No.: US 9,770,469 B2
(45) Date of Patent: Sep. 26, 2017

(54) METHODS OF REPROGRAMMING RENAL CELLS

(71) Applicant: Tel HaShomer Medical Research Infrastructure and Services Ltd., Ramat-Gan (IL)

(72) Inventors: Benjamin Dekel, Tel-Aviv (IL); Orit Harari-Steinberg, RaAnana (IL)

(73) Assignee: Tel HaShomer Medical Research Infrastructure and Services Ltd., Ramat-Gan (IL)

( * ) Notice: Subject to any disclaimer, the term of this patent is extended or adjusted under 35 U.S.C. 154(b) by 389 days.

(21) Appl. No.: 14/027,256

(22) Filed: Sep. 16, 2013

(65) Prior Publication Data

US 2014/0011280 A1    Jan. 9, 2014

Related U.S. Application Data

(62) Division of application No. 13/203,277, filed as application No. PCT/IL2010/000159 on Feb. 25, 2010, now abandoned.

(60) Provisional application No. 61/202,425, filed on Feb. 26, 2009, provisional application No. 61/202,426, filed on Feb. 26, 2009.

(51) Int. Cl.
| | | |
|---|---|---|
| *C12N 5/00* | (2006.01) | |
| *A61K 35/22* | (2015.01) | |
| *C12N 5/071* | (2010.01) | |
| *C12N 5/074* | (2010.01) | |
| *C12N 15/85* | (2006.01) | |

(52) U.S. Cl.
CPC ............ *A61K 35/22* (2013.01); *C12N 5/0686* (2013.01); *C12N 5/0687* (2013.01); *C12N 5/0696* (2013.01); *C12N 15/85* (2013.01); *C12N 2500/90* (2013.01); *C12N 2501/06* (2013.01); *C12N 2501/065* (2013.01); *C12N 2501/415* (2013.01); *C12N 2506/25* (2013.01)

(58) Field of Classification Search
CPC .............................. C12N 5/0687; A61K 35/22
See application file for complete search history.

(56) References Cited

U.S. PATENT DOCUMENTS

| | | |
|---|---|---|
| 2002/0102241 A1 | 8/2002 | Arnaout et al. |
| 2002/0119565 A1 | 8/2002 | Clarke et al. |
| 2004/0014209 A1 | 1/2004 | Lassar et al. |
| 2005/0026023 A1 | 2/2005 | Hirai et al. |
| 2007/0031966 A1 | 2/2007 | Dressler et al. |
| 2007/0065942 A1 | 3/2007 | Wandinger-Ness et al. |
| 2010/0097794 A1 | 4/2010 | Teng et al. |
| 2011/0311494 A1 | 12/2011 | Benjamin et al. |
| 2011/0311495 A1 | 12/2011 | Dekel |
| 2013/0059325 A1 | 3/2013 | Dekel |

FOREIGN PATENT DOCUMENTS

| | | |
|---|---|---|
| WO | WO 2005/021738 | 3/2005 |
| WO | WO 2010/097793 | 9/2010 |

OTHER PUBLICATIONS

Hueber et al. Kidney International 69:1139-1145, 2006.*
Nakagawa et al. Nature Biotechnology 26(1):101-106, 2008.*
Office Action Dated Oct. 27, 2013 From the Israel Patent Office Re. Application No. 214783 and Its Translation Into English.
Communication Pursuant to Article 94(3) EPC Dated Jan. 22, 2014 From the European Patent Office Re. Application No. 11728406.7.
International Preliminary Report on Patentability Dated Nov. 22, 2012 From the International Bureau of WIPO Re. Application No. PCT/IL2011/000376.
International Search Report and the Written Opinion Dated Sep. 26, 2011 From the International Searching Authority Re. Application No. PCT/IL2011/000376.
Official Action Dated Apr. 2, 2014 From the US Patent and Trademark Office Re. U.S. Appl. No. 13/697,531.
Restriction Official Action Dated Dec. 31, 2013 From the US Patent and Trademark Office Re. U.S. Appl. No. 13/697,531.
Supplemental Notice of Allowability Dated Jun. 6, 2014 From the US Patent and Trademark Office Re. U.S. Appl. No. 13/203,282.
Bussolati et al. "Isolation of Renal Progenitor Cells From Adult Human Kidney", American Journal of Pathology, XP002454238, 166(2): 545-555, Feb. 1, 2005.
Buzhor et al. "Kidney Spheroids Recapitulate Tubular Organoids Leading to Enhanced Tubulogenic Potency of Human Kidney-Derived Cells", Tissue Engineering Part A, XP55006582, 17(17-18): 2305-2319, Sep. 1, 2011.
Eccles et al. "Comparative In Situ Hybridization Analysis of PAX2, PAX8, and WT1 Gene Transcription in Human Fetal Kidney and Wilms' Tumors", American Journal of Pathology, 146(1): 40-45, Jan. 1995.
Garvin et al. "The In Vitro Growth, Heterotransplantation, and Immunohistochemical Characterization of the Bleastemal Component of Wilms' Tumor", American Journal of Pathology, 129(2): 353-363, Nov. 1987.
Liu et al. "Suspended Aggregates as an Immobilization Mode for High-Density Perfusion Culture of HEK 293 Cells in a Stirred Tank Bioreactor", Applied Microbiology and Biotechnology, XP019441688, 72(6): 1144-1151, Mar. 28, 2006. p. 1147, Table 1.
Lusis et al. "Isolation of Clonogenic, Long-Term Self Renewing Embryonic Renal Stem Cells", Stem Cell Research, XP027106369, 5(1): 23-29, Mar. 27, 2010. p. 27.
Maeshima et al. "Adult Kidney Tubular Cell Population Showing Phenotypic Plasticity, Tubulogenic Capacity, and Integration Capability Into Developing Kidney", Journal of the American Society of Nephrology, XP002471868, 17(1): 188-198, Jan. 1, 2006.

(Continued)

*Primary Examiner* — Marcia S Noble

(57) ABSTRACT

A method of reprogramming a differentiated renal cell towards a progenitor phenotype is disclosed. The method comprises up-regulating in the differentiated renal cell an expression of at least one pluripotency associated gene and/or at least one renal stem cell associated gene, thereby reprogramming the differentiated renal cell towards a progenitor phenotype. Cell populations generated thereby and uses thereof are also disclosed.

7 Claims, 20 Drawing Sheets
(2 of 20 Drawing Sheet(s) Filed in Color)

(56) References Cited

OTHER PUBLICATIONS

Metsuyanim et al. "Accumulation of Malignant Renal Stem Cells is Associated With Epigenetic Changes in Normal Renal Progenitor Genes", Stem Cells, XP002658726, 26(7): 1808-1817, 2008.
Pode-Shakked et al. "Development Tumourigenesis: NCAM as a Putative Marker for the Malignant Renal Stem/Progenitor Cell Population", Journal of Cellular and Molecular Medicine, XP002581529, 13(8B): 1792-1808, Aug. 1, 2009. p. 1795, r-h Col., Fig.1.
Official Action Dated Sep. 12, 2014 From the US Patent and Trademark Office Re. U.S. Appl. No. 13/697,531.
Official Action Dated Mar. 23, 2015 US Patent and Trademark Office Re. U.S. Appl. No. 13/697,531.
Gibson-D'Ambrosio et al. "Characteristics of long-term human epithelial cell cultures derived from normal human fetal kidney". In Vitro Cell Development and Biology, 23(4): 279-287, Apr. 1987. Abstract.
Communication Pursuant to Article 94(3) EPC Dated Mar. 27, 2015 From the European Patent Office Re. Application 10710685.8.
Communication Pursuant to Article 94(3) EPC Dated Mar. 27, 2015 From the European Patent Office Re. Application No. 10712582.5.
Communication Pursuant to Article 94(3) EPC Dated Mar. 27, 2015 From the European Patent Office Re. Application No. 11188963.0.
Office Action Dated Oct. 9, 2013 From the Israel Patent Office Re. Application No. 216043 and Its Translation Into English.
Office Action Dated Oct. 7, 2013 From the Israel Patent Office Re. Application No. 214837 and Its Translation Into English.
Communication Pursuant to Article 94(3) EPC Dated Jan. 28, 2013 From the European Patent Office Re. Application 10710685.8.
Communication Pursuant to Article 94(3) EPC Dated Jan. 28, 2013 From the European Patent Office Re. Application No. 10712582.5.
Communication Pursuant to Rules 70(2) and 70a(2) EPC and Reference to Rule 39(1) EPC Dated Mar. 4, 2013 From the European Patent Office Re. Application No. 11188963.0.
Communication Relating to the Results of the Partial International Search Dated Jun. 28, 2010 From the International Searching Authority Re. Application No. PCT/IL2010/000158.
European Search Report and the European Search Opinion Dated Jan. 24, 2013 From the European Patent Office Re. Application No. 11188963.0.
International Preliminary Report on Patentability Dated Sep. 9, 2011 From the International Bureau of WIPO Authority Re. Application No. PCT/IL2010/000158.
International Preliminary Report on Patentability Dated Sep. 9, 2011 From the International Bureau of WIPO Re. Application No. PCT/IL2010/000159.
International Search Report and the Written Opinion Dated Oct. 11, 2010 From the International Searching Authority Re. Application No. PCT/IL2010/000158.
International Search Report and the Written Opinion Dated Jun. 18, 2010 From the International Searching Authority Re. Application No. PCT/IL2010/000159.
Official Action Dated Aug. 8, 2013 From the US Patent and Trademark Office Re. U.S. Appl. No. 13/203,282.
Official Action Dated May 16, 2013 From the US Patent and Trademark Office Re. U.S. Appl. No. 13/203,277.
Restriction Official Action Dated Apr. 11, 2013 From the US Patent and Trademark Office Re. U.S. Appl. No. 13/203,282.
Restriction Official Action Dated Feb. 25, 2013 From the Re. U.S. Appl. No. 13/203,277.
Alison et al. "Attributes of Adult Stem Cells", The Journal of Pathology, XP002602081, 217(2): 144-160, Jan. 2009. p. 149.
Araki et al. "Chromatin-Modifying Agents Permit Human Hematopoietic Stem Cells to Undergo Multiple Cell Divisions While Retaining Their Repopulating Potential", Blood, XP002583271, 109(8): 3570-3578, Apr. 15, 2007. p. 3570-3571.
Balzar et al. "The Biology of the 17-1A Antigen (Ep-CAM)", The Journal of Molecular Medicine, 77: 699-712, 1999.
Boyle et al. "Fate Mapping Using Cited1-CreERT2 Mice Demonstrates That the Cap Mesenchyme Contains Self-Renewing Progenitor Cells and Gives Rise Exclusively to Nephronic Epithelia", Developmental Biology, 313: 234-245, 2008.
Brodbeck et al. "Genetic Determination of Nephrogenesis: The Pax/Eya/Six Gene Network", Pediatric and Nephrology, 19: 249-255, 2004. Abstract.
Chang et al. Cancer Research, 47: 1634-1645, 1987.
Cirulli et al. "E-Cadherin, NCAM, and EpCAM Expression in Human Fetal Pancreata", Transplantation Proceedings, 27(6): 3335, Dec. 1995.
Dekel et al. "Applications of Tissue Engineering for the Treatment of Renal and Urogenital Disease", 208, 2006.
Dekel et al. "Engraftment and Differentiation of Human Metanephroi Into Functional Mature Nephrons After Transplantation Into Mice Is Accompanied by a Profile of Gene Expression Similar to Normal Human Kidney Development", Journal of the American Society of Nephrology, 13: 977-990, 2002.
Dekel et al. "Engraftment of Human Kidney Tissue in Rat Radiation Chimera: II. Human Fetal Kidneys Display Reduced Immunogenicity to Adoptively Transferred Human Peripheral Blood Mononuclear Cells and Exhibit Rapid Growth and Development", Transplantation, 64: 1550-1558, 1997. Abstract.
Dekel et al. "Human and Porcine Early Kidney Presursors as a New Source for Transplantation", Nature Medicine, 9: 53-60, 2003. Abstract.
Dekel et al. "Multiple Imprinted and Stemness Genes Provide a Link Between Normal and Tumor Progenitor Cells of the Developing Human Kidney", Cancer Research, XP002581965, 66(12): 6040-6049, Jun. 2006. p. 6040, Table 1.
Douville et al. "ALDH1 as a Functional Marker of Cancer Stem and Progenitor Cells", Stem Cells and Development., XP002602080, 18(1): 17-25, Jan. 2009.
Gibson-D'Ambrosio et al. In Vitro Cell Development and Biology, 23(4): 279-287, Apr. 1987.
Hipp et al. "Sources of Stem Cells for Regenerative Medicine", Stem Cell Reviews, XP002583273, 4(1): 3-11, Apr. 2008. p. 7-8.
Hjelle et al. "Drug Metabolism in Isolated Proximal Tubule Cells: Aldehyde Dehydrogenase", Journal of Pharmacology and Experimental Therapeutics, XP009139110, 224(3): 699-706, Mar. 1, 1983.
Huangfu et al. "Induction of Pluripotent Stem Cells by Defined Factors is Greatly Improved by Small-Molecule Compounds", Nature Biotechnology, XP002502536, 26(7): 795-797, Jul. 1, 2008. p. 795-796.
Imai et al. "Inhibition of histone Deacetylase Activates Side Population Cells in Kidney and Partially Reverses Chronic Renal Injury", Stem Cells, XP002583269, 25(10): 2469-2475, 2007. p. 2469, 2473.
Jones et al. "Genomics of Renal Cell Cancer: The Biology Behind and the Therapy Ahead", Clinical Cancer Research, 13(2 Suppl.): 685s-692s, Jan. 15, 2007.
Kim et al. "Improvement of Kidney Failure With Fetal Kidney Precursor Cell Transplantation", Transplantation, 83: 1249-1258, 2007.
Kim et al. "Kidney Tissue Reconstruction by Fetal Kidney Cell Transplantation: Effect of Gestation Stage of Fetal Kidney Cells", Stem Cells, 25: 1393-1401, 2007.
Kobayashi et al. "Six2 Defines and Regulates a Multipotent Self-Renewing Nephron Progenitor Population Throughout Mammalian Kidney Development", Cell Stem Cell, 3: 169-181, 2008.
Kreidberg et al. "WT-1 Is Required for Early Kidney Development", Cell, 74: 679-691, 1993. Abstract.
Kretzler et al. "Integin-Linked Kinase as a Candidate Downstream Effector in Proteinuria", The FASEB Journal, 15(10): 1843-1845, Aug. 2001.
Markovic-Lipkovski et al. "Neural Cell Adhesion Molecule Expression on Renal Interstitial Cells", Nephrology Dialysis Transplantation, XP002581531, 22(6): 1558-1566, Jun. 2007. p. 1558, 1562-1565.
Metsuyanim et al. "Accumulation of Malignant Renal Stem Cells is Associated With Epigenetic Changes in Normal Renal Progenitor Genes", Stem Cells, 26: 1808-1817, 2008. Abstract.
Metsuyanim et al. "Expression of Stem Cell Markers in the Human Fetal Kidney", PLoS ONE, XP002581532, 4(8): e6709-1-e6709-15, Aug. 2009.

(56) References Cited

OTHER PUBLICATIONS

Milutinovic et al. "Valproate Induces Widespread Epigenetic Reprogramming Which Involves Demethylation of Specific Genes", Carcinogenesis, 28(3): 560-571, 2007.
Miyamoto et al. "Cell-Free Extracts From Mammalian Oocytes Partially Induce Nuclear Reprogramming in Somatic Cells", Biology of Reproduction, XP002583272, 80(5): 935-943, May 1, 2009. p. 936, 939.
Nishinakamura "Kidney Development Conserved Over Species: Essential Roles of Sall1", Seminars in Cell Development and Biology, 14: 241-247, 2003. Abstract.
Osafune et al. "Identification of Multipotent Progenitors in the Embryonic Mouse Kidney by a Novel Colony-Forming Assay", Development, XP002581530, 133(1): 151-161, Jan. 2006. p. 153, Fig. 1.
Pode-Shakked et al. "Developmental Tumourigenesis: NCAM as a Putative Marker for the Malignant Renal Stem/Progenitor Cell Population", Journal of Cellular and Molecular Medicine, XP002581529, 13(8B): 1792-1808, Dec. 16, 2008. p. 1792-1793, 1797.
Rivera et al. "Wilm's Tumor: Connecting Tumorigenesis and Organ Development in the Kidney", Nature Reviews: Cancer, 5: 699-712, 2005.
Rosenberg et al. "Stem Cells and the Kidney: Where Do We Go From Here?", Journal of the American Society of Nephrology, XP002581964, 18(12): 3018-3020, Dec. 2007. p. 3019.
Schmelzer et al. "The Phenotypes of Pluripotent Human Hepatic Progenitors", Stem Cells, XP002581966, 24(8): 1852-1858, Aug. 2006.
Schmidt-Ott et al. "WNT/Beta-Catenin Signaling in Nephron Progenitors and Their Epithelial Progeny", Kidney International, XP002602079, 74(8): 1004-1008, Oct. 2008.
Self et al. "Six2 is Required for Suppression of Nephrogenesis and Progenitor Renewal in the Developing Kidney", The EMBO Journal, 25: 5214-5228, 2006.
Senanayake et al. "The Pluripotent Renal Stem Cell Regulator SIX2 is Activated in Renal Neoplasms and Influences Cellular Proliferation and Migration", Human Pathology, 44: 336-345, 2013.
Trzpis et al. "Epithelial Cell Adhesion Molecule—More Than a Carcinoma Marker and Adhesion Molecule", The American Journal of Pathology, XP002581967, 171(2): 386-395, Aug. 2007. p. 388-389, Table 2.
Trzpis et al. "Expression of EpCAM is Up-Regulated During Regeneration of Renal Epithelia", Journal of Pathology, XP002581968, 216(2): 201-208, Oct. 2008.
Weissmann "Translating Stem and Progenitor Cell Biology to the Clinic: Barriers and Opportunities", Science, 287(5457): 1442-1446, 2000. Abstract.
Xu et al. Principles of Tissue Engineering, 2000.
Yoshikawa et al. "Inhibition of Histone Deacetylase Activity Suppresses Epithelial-to-Mesenchymal Transition Induced by TGF-?1 in Human Renal Epithelial Cells", Journal of the American Society of Nephrology, XP002583270, 18(1): 58-65, Jan. 2007. p. 58.
Yoshikawa et al. "Inhibition of Histone Deacetylase Activity Suppresses Epithelial-to-Mesenchymal Transition Induced by TGF-Beta1 in Human Renal Epithelial Cells", Journal of the American Society of Nephrology, JASN, 18(1): 58-65, Jan. 2007.
Communication Pursuant to Article 94(3) EPC Dated Dec. 19, 2014 From the European Patent Office Re. Application No. 11728406.7.
Zhong et al. "Spheres Derived From the Human SK-RC-42 Renal Cell Carcinoma Cell Line Are Enriched in Cancer Stem Cells", Cancer Letters, XP027451196, 299(2): 150-160, Dec. 28, 2010.

\* cited by examiner

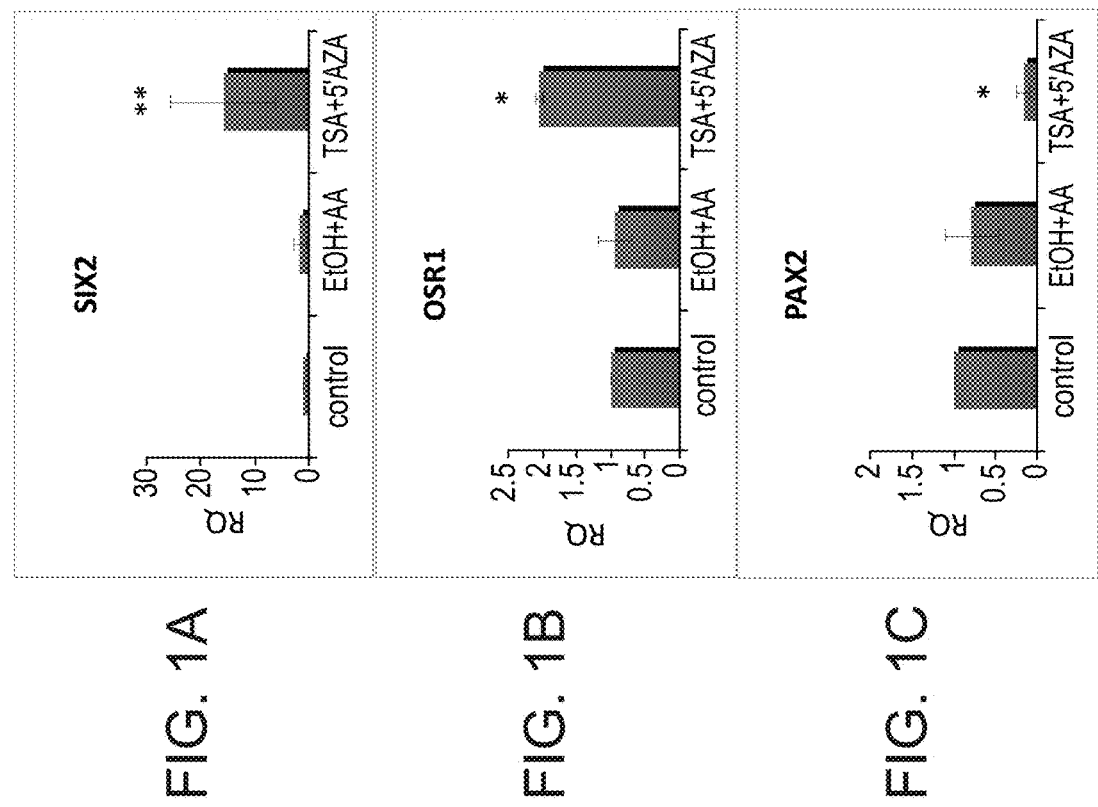

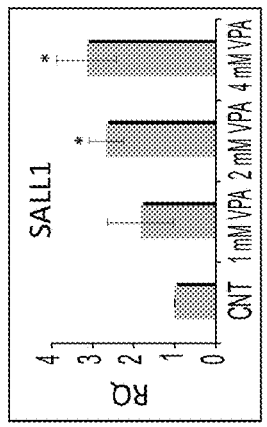
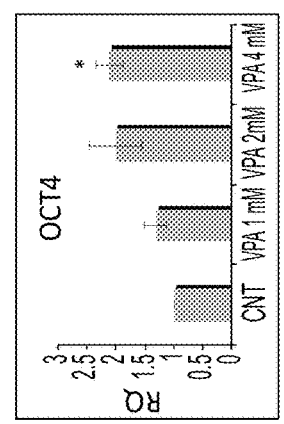
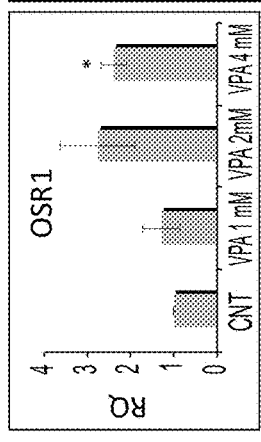
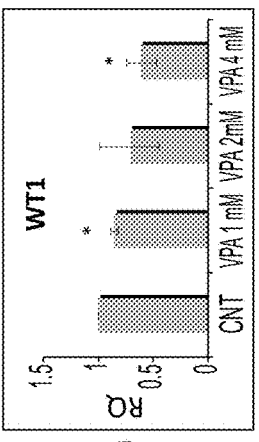
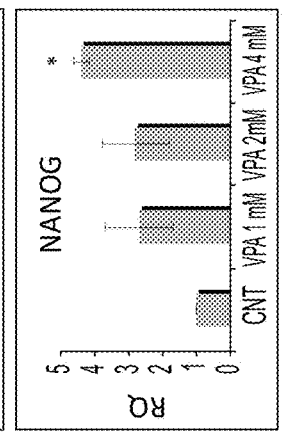
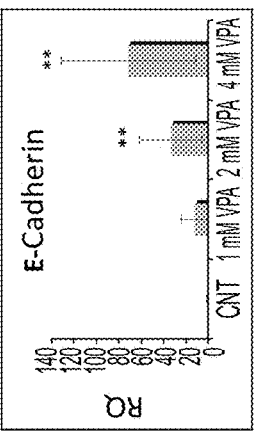
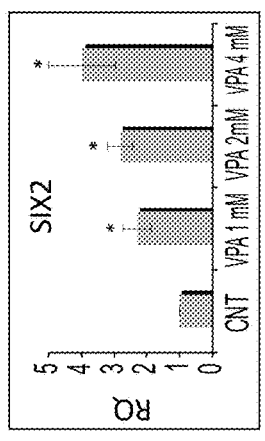
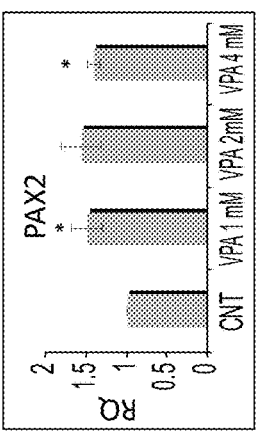
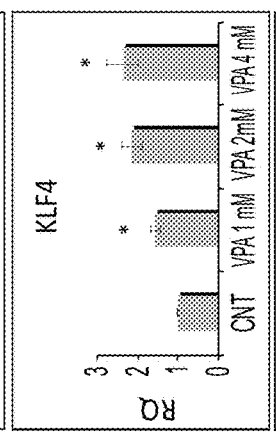
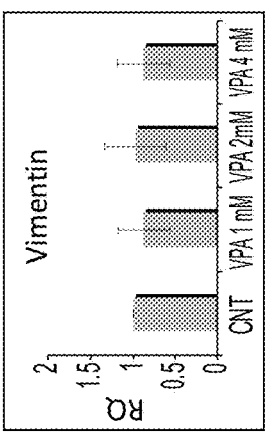

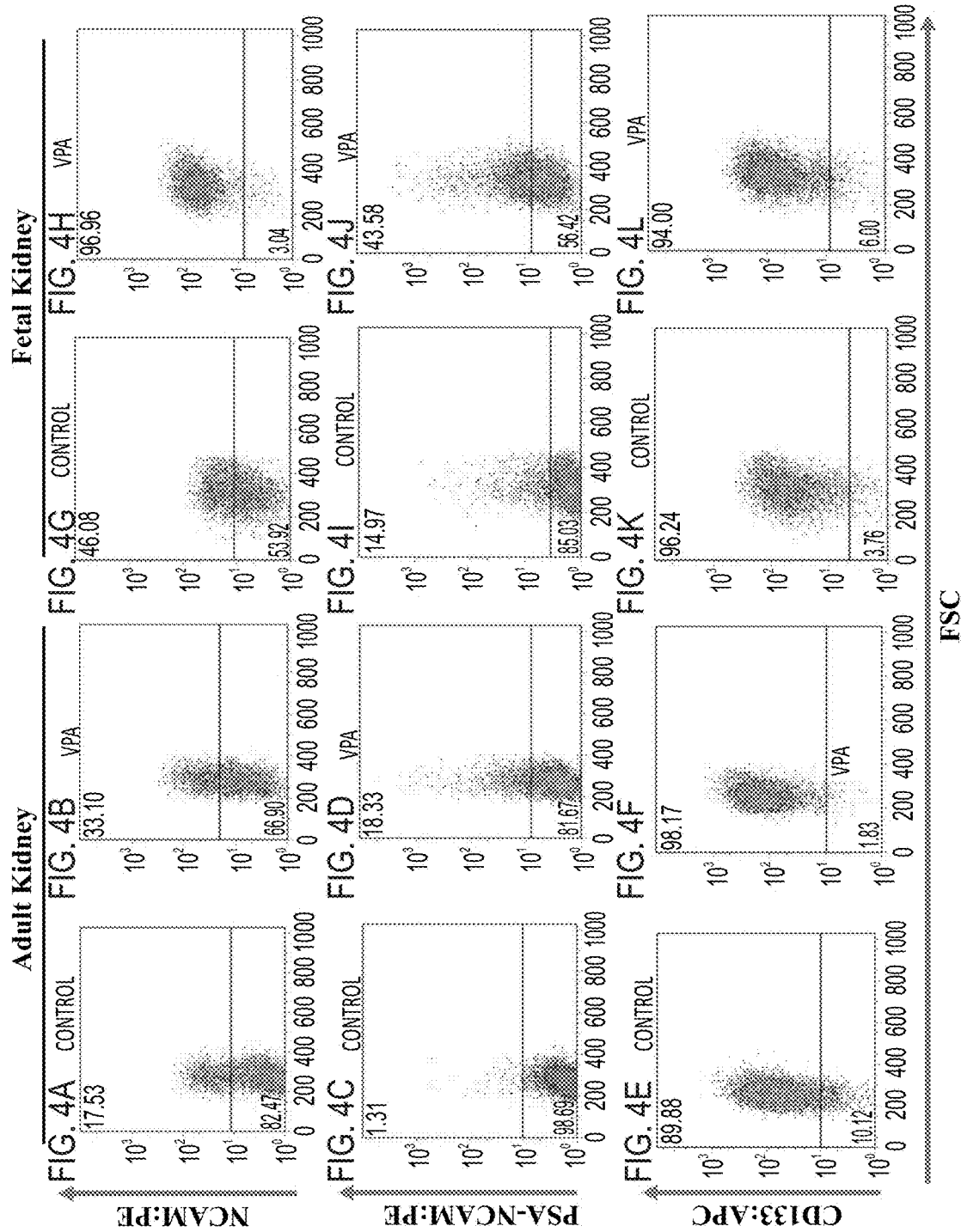

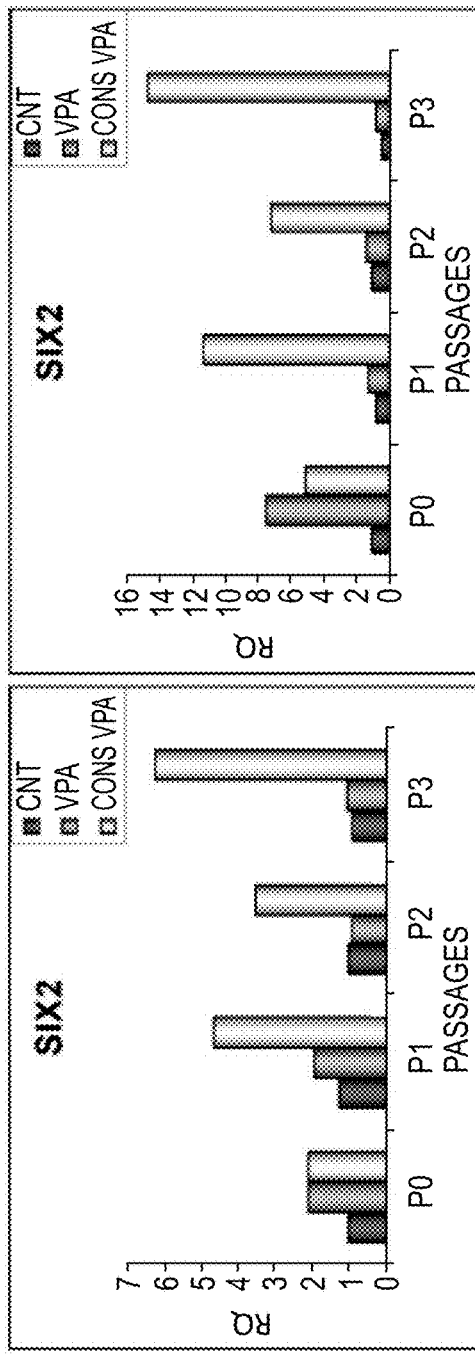
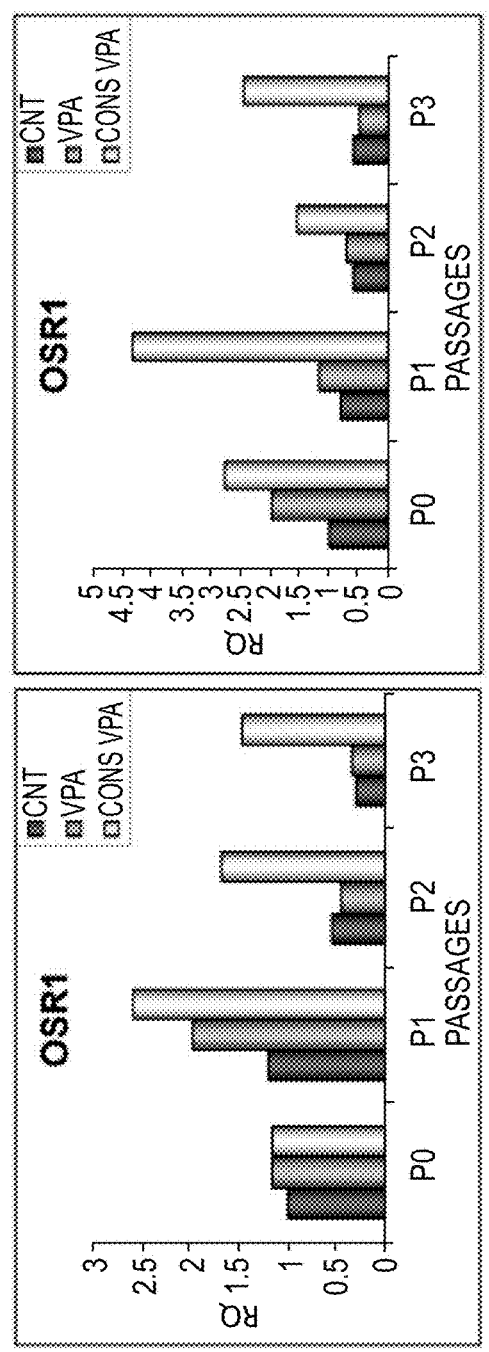
FIG. 5A  FIG. 5B  FIG. 5C  FIG. 5D

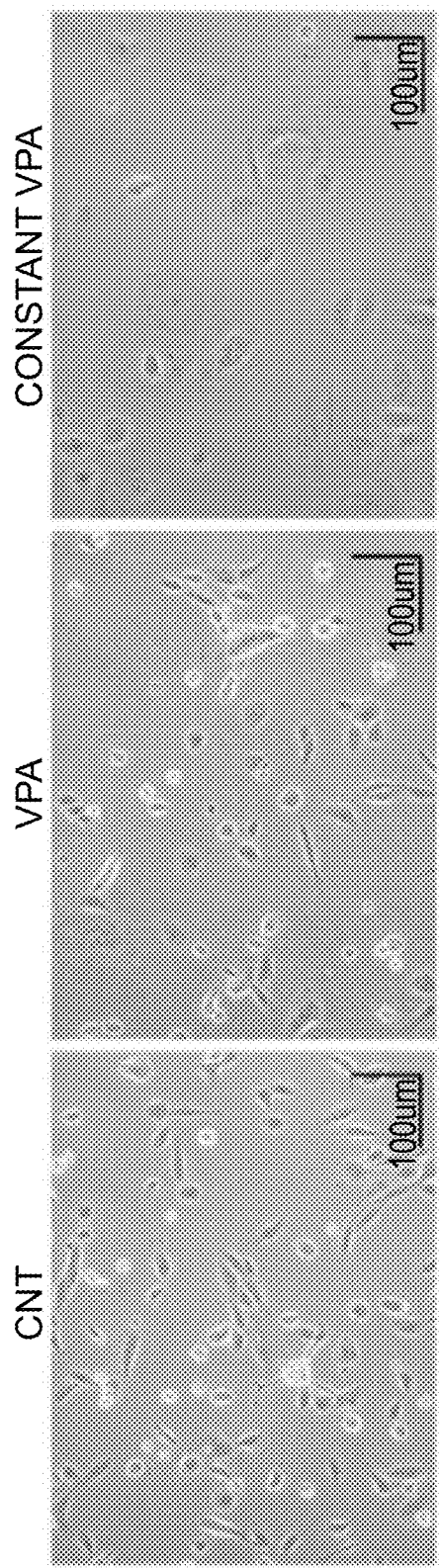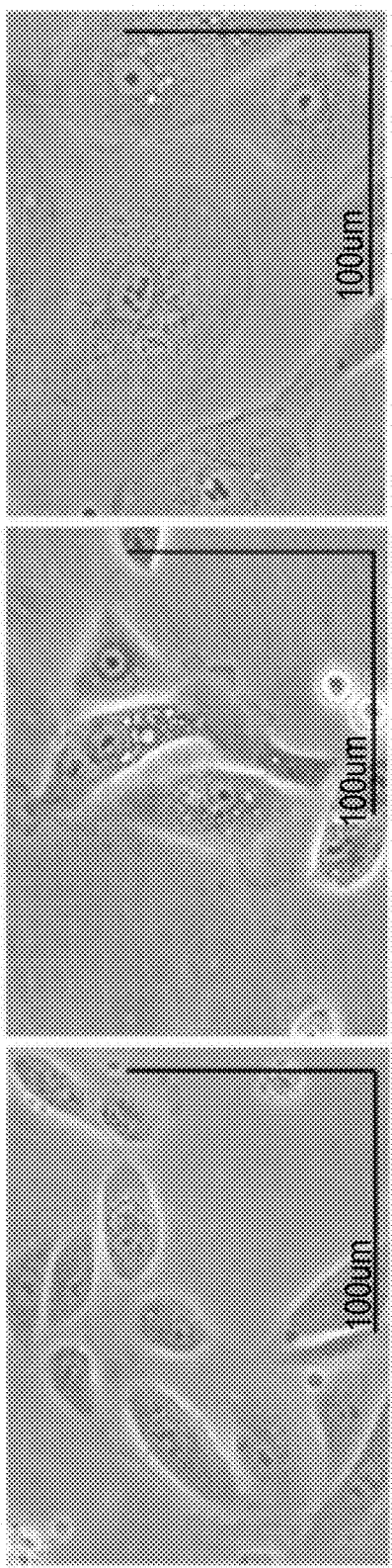

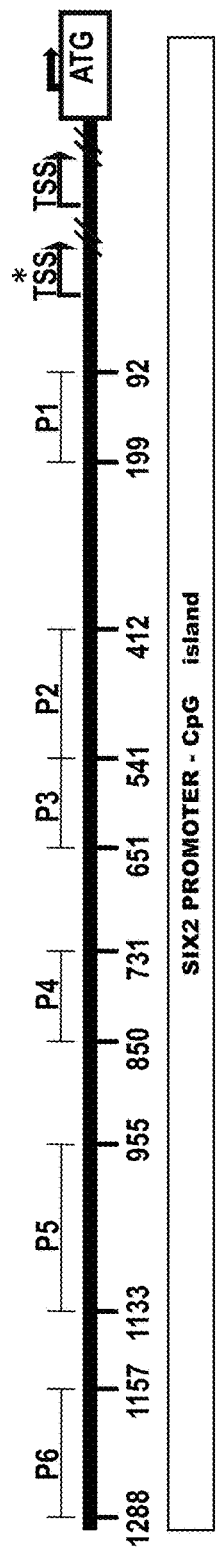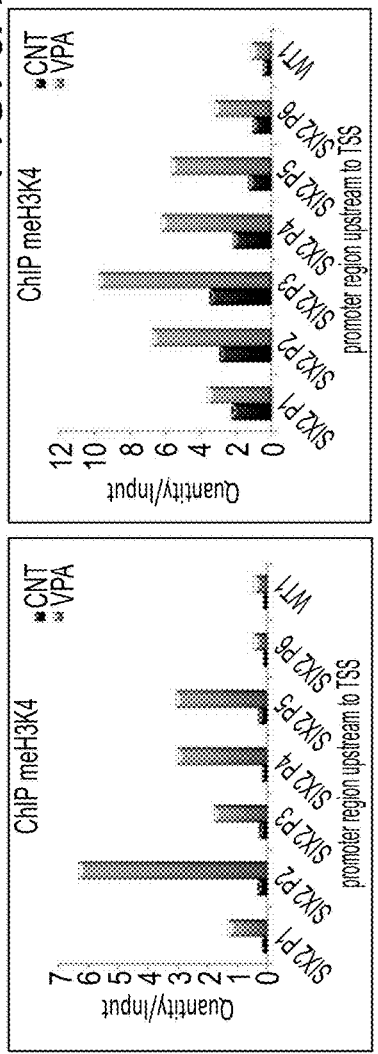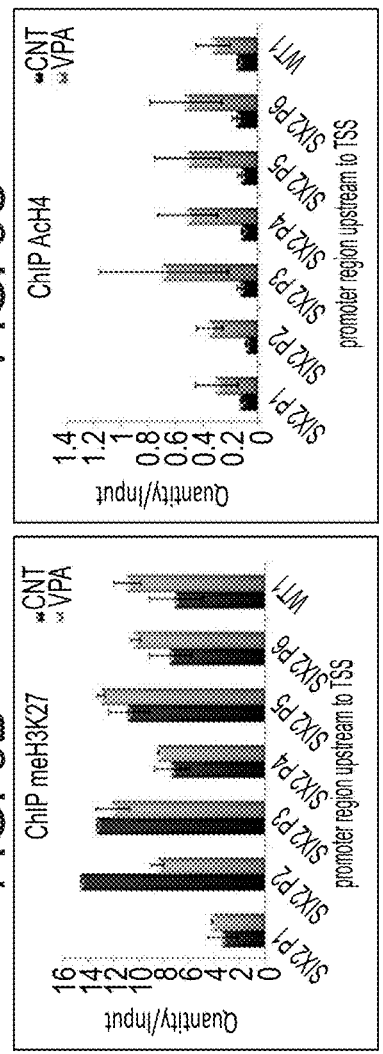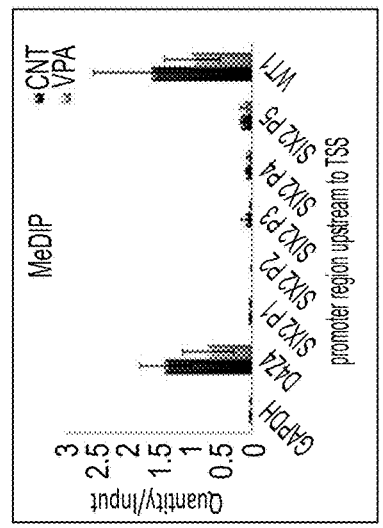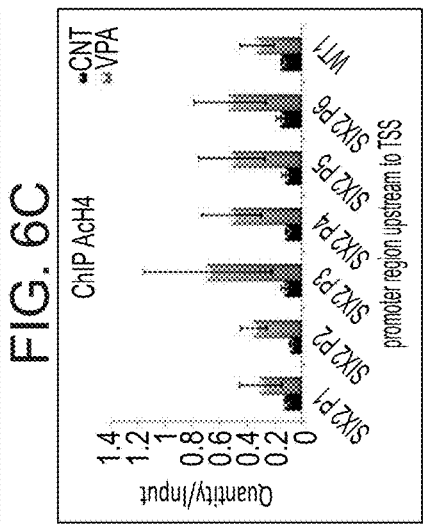

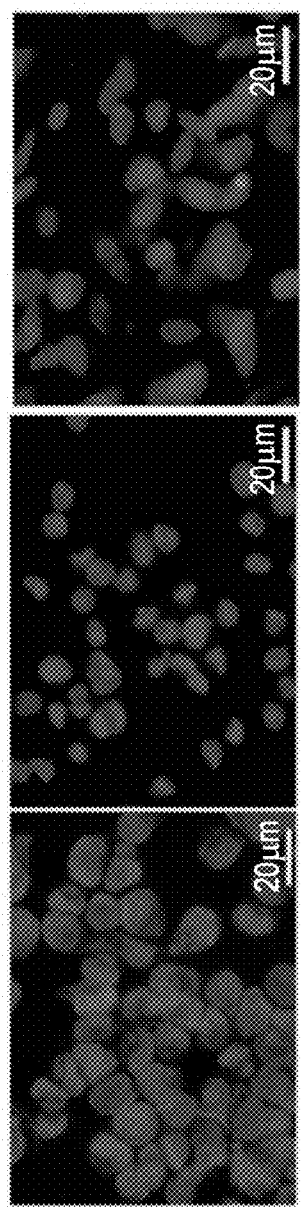
FIG. 7C    FIG. 7D    FIG. 7E
FIG. 7F
FIG. 7G
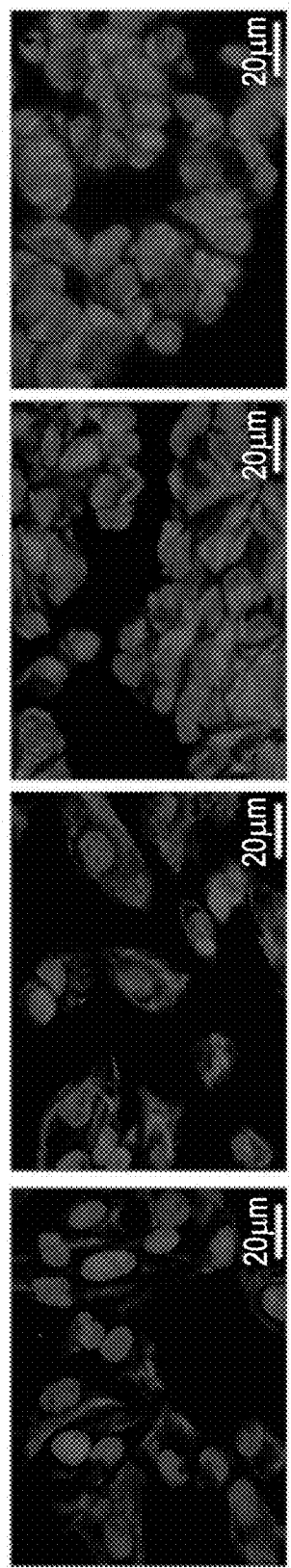
FIG. 7H
FIG. 7J
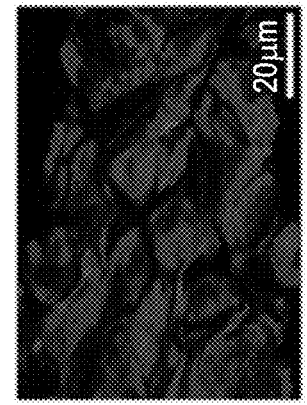
FIG. 7I
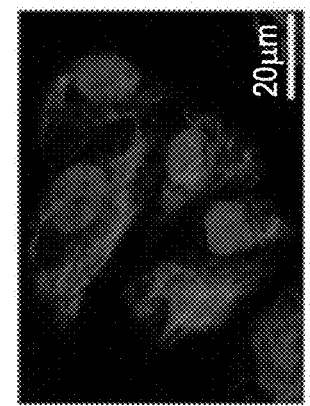
FIG. 7K
FIG. 7L
FIG. 7M

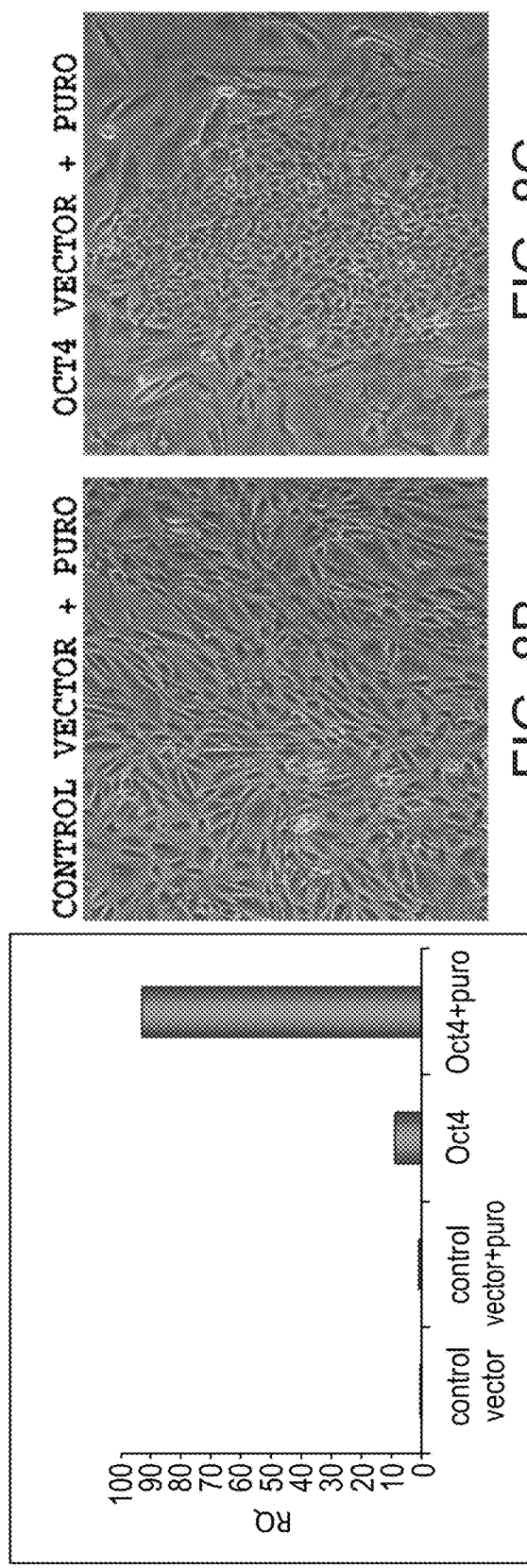

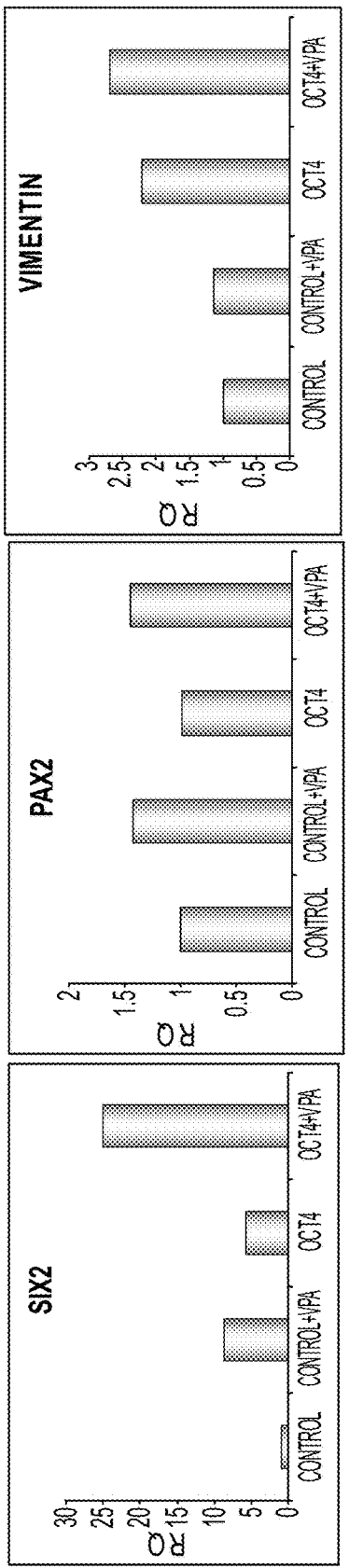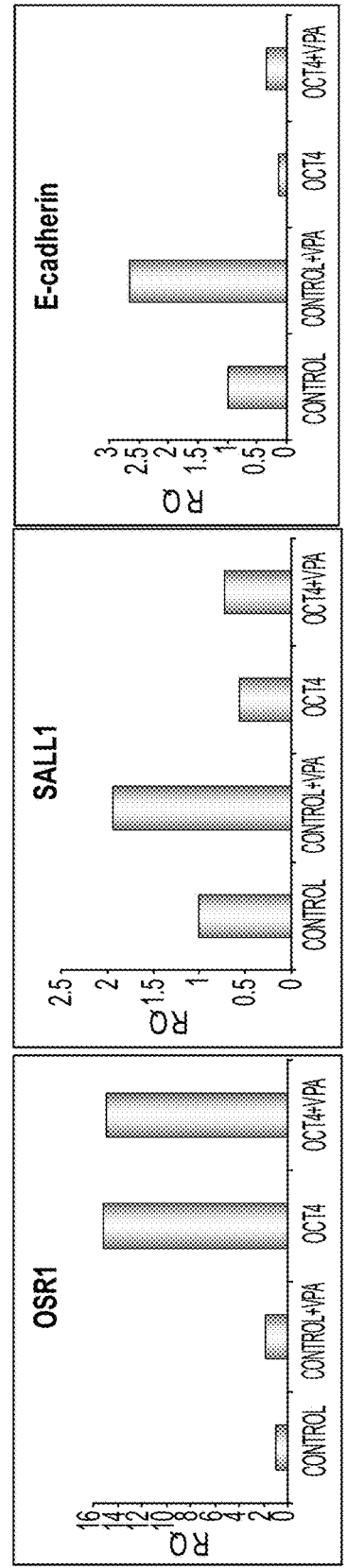
FIG. 9A FIG. 9B FIG. 9C
FIG. 9D FIG. 9E FIG. 9F

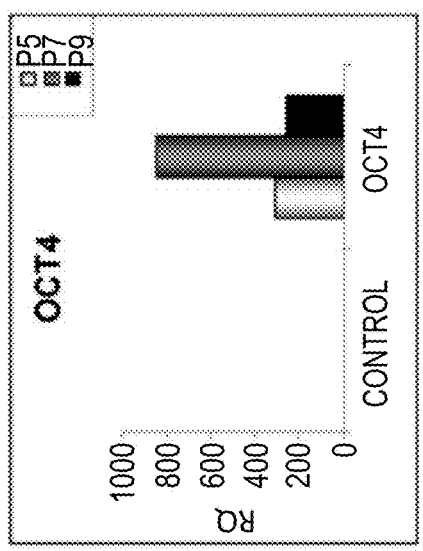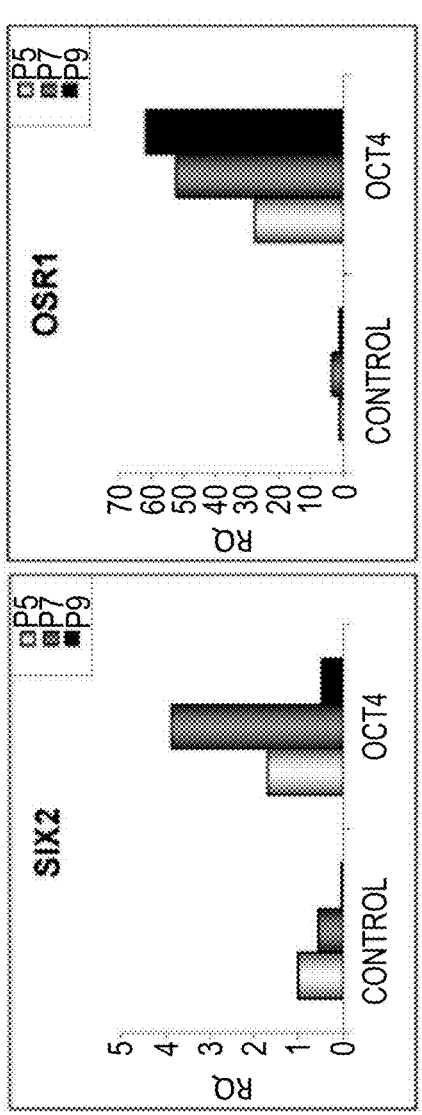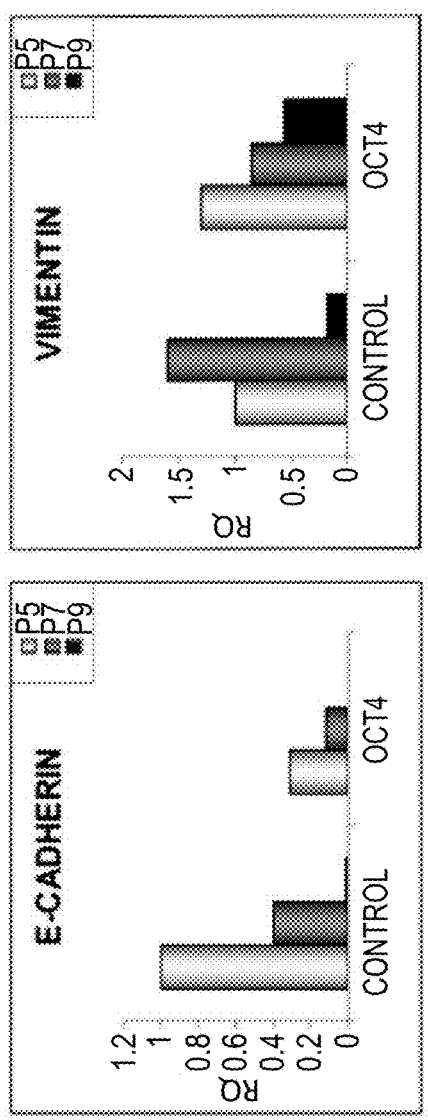
FIG. 11A  FIG. 11B  FIG. 11C  FIG. 11D  FIG. 11E

METHODS OF REPROGRAMMING RENAL CELLS

RELATED APPLICATIONS

This application is a division of U.S. patent application Ser. No. 13/203,277 filed on Aug. 25, 2011, which is a National Phase of PCT Patent Application No. PCT/IL2010/000159 having International filing date of Feb. 25, 2010, which claims the benefit of priority of U.S. Provisional Patent Application Nos. 61/202,425 and 61/202,426 both filed on Feb. 26, 2009. The contents of the above applications are all incorporated herein by reference.

SEQUENCE LISTING STATEMENT

The ASCII file, entitled 57479SequenceListing.txt, created on Sep. 12, 2013, comprising 49,664 bytes, submitted concurrently with the filing of this application is incorporated herein by reference.

FIELD AND BACKGROUND OF THE INVENTION

The present invention, in some embodiments thereof, relates to isolated populations of renal progenitor cells and methods of generating and using same.

The fundamental functional unit of the kidney required for urine formation is the nephron. The number of nephrons in the human adult kidney (HAK) ranges from 300,000 to a million. The human metanephros (direct embryonic precursor tissue of the adult kidney) appears at the 5$^{th}$ week of gestation and renal stem/progenitor cells in a discrete region of the metanephros termed the metanephric/nephrogenic mesenchyme (MM) are induced to undergo mesenchymal-to-epithelial transition (MET) and form all epithelial cell types of the nephron until 34 weeks of gestation. These include glomerular (parietal, visceral) and tubular (proximal, distal) epithelia (which can be detected by segment-specific markers) but not collecting ducts. Thus, endowment of new nephrons is restricted to prenatal development in humans, while in rodents it persists only until the immediate postnatal period (up to 2 weeks postnatal).

Specifying the renal progenitor population throughout development are a unique combination of transcription factors, including the Hox11 paralogs, Osr1, Pax2, Eya1, Wt1, Sall1, Six2, and Cited1. These genes considered early markers of kidney progenitor cells are silenced, at least in part, by epigenetic modifications once nephrogenesis commences [1]. Epigenetic modifications responsible for transcriptional and lineage control are reversible and can be therefore manipulated. For example: methylation of lysine 27 on histone subunit H3 (H3K27me) by the Polycomb complex is associated with transcriptional repression, whereas methylation of lysine 4 on H3 (H3K4me) and any lysine acetylation of histones is associated with gene activation. Of all, recent experiments have established that Six2 and Osr1 are required to sustain a true committed stem cell in the MM that is capable of self-renewing and of differentiating towards different types of nephron epithelia [2-4].

Genetic diseases affecting the various cell types of the nephron are the leading cause of end-stage renal disease (ESRD) in the pediatric population which requires renal replacement therapy (dialysis, transplantation) and carries extremely high morbidity and mortality rates. Mutations in genes that specify the renal progenitor cell pool (see above) can lead to either congenital renal hypoplasia (too few nephrons) or to the appearance of malformed nephrons (congenital renal dysplasia). These can be viewed as 'kidney stem cell diseases'. In contrast, mutations in genes that participate in the function of a highly specialized cell type in the kidney result in loss of that specific task. One such example are genetic defects in structural proteins of the glomerular podocyte (podocin, nephrin), an epithelial cell type responsible for the filtration barrier, which lead to massive spillage of protein to the urine and to the appearance of nephrotic syndrome, focal segmental glomerulosclerosis and ESRD (ref). In contrast to acquired childhood nephrotic syndrome which is sensitive to steroid treatment, the inherited disease is steroid-resistant.

The goal of renal regenerative medicine is to create an unlimited supply of human cells resembling the renal progenitors residing in the MM so as be able to replenish diseased ones in renal hypoplasia/dysplasia, affording enhanced nephron development or replace glomerular podocytes by inoculating a cell population containing the podocyte progenitor cell.

Derivation of renal stem/progenitors can be achieved by various strategies. One strategy is to sort them out from developing human kidneys via specific surface markers (similar to hematopoietic stem cells of the hematopoietic system). Another strategy is to induce differentiation of pluripotent cells (allogeneic human ES) along the renal lineage. A third strategy is to dedifferentiate autologous cell sources such as human adult kidney (HAK) cells into renal stem/progenitors.

Yamanaka and colleagues have shown the ability to reprogram cells into a pluripotent phenotype via the overexpression of specific factors, Oct4, c-Myc, Sox2, Klf4 [5]. Recently, Melton and colleagues reported the in vivo reprogramming of adult pancreatic exocrine cells to beta-cells using a strategy of re-expressing key developmental regulators of the endocrine pancreas [6], indicating a general paradigm for directing cell reprogramming and trans-differentiation across two mature cell types without reversion to a pluripotent stem cell state.

Metsuyanim et al teaches that the cessation of nephrogenesis is coincident with dramatic down-regulation of the renal progenitor genes, which is associated in part with epigenetic silencing [1].

U.S. Patent Application No. 20060177925 teaches multipotent renal progenitor cells (MRPC) that are antigen positive for vimentin and Oct-4, and are antigen negative for zona occludens, cytokeratin, and major histocompatibility Class I and II molecules.

SUMMARY OF THE INVENTION

According to an aspect of some embodiments of the present invention there is provided a method of reprogramming a differentiated renal cell towards a progenitor phenotype, the method comprising up-regulating in the differentiated renal cell an expression of at least one pluripotency associated gene and/or at least one renal stem cell associated gene, thereby reprogramming the differentiated renal cell towards a progenitor phenotype.

According to an aspect of some embodiments of the present invention there is provided a renal cell population generated according to the method of the present invention.

According to an aspect of some embodiments of the present invention there is provided a method of repairing or regenerating a renal tissue in a subject in need thereof the method comprising administering to the subject a therapeutically effective amount of the renal cell population of the present invention, thereby repairing or regenerating renal tissue in a subject.

According to an aspect of some embodiments of the present invention there is provided a method of monitoring differentiation state of a renal cell, the method comprising determining in the renal cell expression of a pluripotency associated gene selected from the group consisting of Oct4, Nanog and klf4, and/or at least one renal stem cell associated gene selected from the group consisting of Six2, Osr1, Pax2, Sal1 and cited 1, wherein expression of the gene above a predetermined threshold is indicative of a renal stem cell.

According to an aspect of some embodiments of the present invention there is provided a use of the renal cell population of the present invention, for the preparation of a medicament for the treatment of a renal disorder.

According to an aspect of some embodiments of the present invention there is provided a method of monitoring differentiation state of a renal cell, the method comprising determining in the renal cell expression of a pluripotency associated gene selected from the group consisting of Oct4, Nanog and klf4, and/or at least one renal stem cell associated gene selected from the group consisting of Six2, Osr1, Pax2, Sal1 and cited 1, wherein expression of the gene above a predetermined threshold is indicative of a renal stem cell.

According to some embodiments of the invention, the method further comprises isolating the cell with the progenitor phenotype.

According to some embodiments of the invention, the at least one pluripotency associated gene is selected from the group consisting of Oct4, Nanog and klf4.

According to some embodiments of the invention, the at least one renal stem cell associated gene is selected from the group consisting of Six2, Osr1, Pax2, Sal1 and cited 1.

According to some embodiments of the invention, the upregulating is effected by contacting the differentiated renal cell with at least one chromatin modifying agent.

According to some embodiments of the invention, the upregulating is effected by transfecting the differentiated renal cell with a nucleic acid construct comprising a nucleic acid sequence of the at least one pluripotency associated gene and/or the at least one renal stem cell associated gene.

According to some embodiments of the invention, the at least one chromatin modifying agent is selected from the group consisting of valproic acid, 5-aza-2'-deoxycytidine and TSA.

According to some embodiments of the invention, the differentiated renal cell is a human differentiated renal cell.

According to some embodiments of the invention, the differentiated renal cell is an adult differentiated renal cell.

According to some embodiments of the invention, the method further comprises contacting the differentiated renal cell with a Wnt antagonist.

According to some embodiments of the invention, the method further comprises isolating the renal stem cell.

According to some embodiments of the invention, the renal cell is a human renal cell.

According to some embodiments of the invention, the renal cell is an adult renal cell.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawings will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIGS. 5A-D are graphs illustrating temporal expression patterns of Six2 and Osr1 mRNA in HAK cells undergoing culture passages and subjected to constant VPA exposure (const VPA), 24-hour exposure to 4 mM VPA (VPA) and control samples (CNT). Total RNA was isolated from the HAK cells in P1-P3 and transcript levels of were analyzed by qRT-PCR. Shown are two examples of independent human kidney cells.

FIGS. 5E-J are photographs illustrating epithelial-like cell morphology in VPA constant treated cells compared to fibroblastic appearance in transient VPA exposure and control groups.

FIG. 6A is a scheme of CpG island region in the Six2 promoter. Marked sections refer to the tested region upstream to the stared transcription starting site (TSS) (the un-stared TSS is an alternative one).

FIGS. 6B-F are bar graphs illustrating the results of CHIP assays. FIG. 6B-E: Comparison of histone modifications between VPA treated and untreated human kidney cells. DNA immunoprecipitated with antibodies directed against meH3K4, meH3K27 and AcH4 was analyzed by qRT-PCR utilizing primers from different regions of the Six2 promoter and one region of the Wt1 promoter. To evaluate the level of histone acetylation and methylation, the ratio of PCR products from immunoprecipitated DNA vs. input DNA was calculated. CHIP assays for meH3K4 are shown using two different antibodies. FIG. 6F: Methylation state of the Six2 promoter was analyzed by MeDIP; GAPDH was used as negative control and D4Z4 as positive control. To evaluate the level of DNA methylation, the ratio of PCR products from immunoprecipitated DNA vs. input DNA was calculated.

FIGS. 7C-M are photographs illustrating β-catenin immunofluorescence in adult and fetal kidney after treatment with valproic acid for 24 hours; Human epithelial cell line with (C) or without (D) primary antibody was used as positive or antibody control, respectively. Human fibroblast cell line (E) was used as negative control. β-catenin expression in adult or fetal kidney before (F, G and H, I) and after (J, K and L, M) treatment, respectively is shown in low (×63) and high magnification (×100), showing strong and extensive expression in VPA treated cells, as well as nuclear localization in the adult kidney (J). Bar represents 20 μM and cell nucleus was stained with Hoechst 33342 (Blue) in all samples tested.

FIGS. 8A-C are graphs and photographs illustrating Overexpression (OE) of Oct4 pluripotency gene in HAK cells. Human Oct4 gene was introduced into HAK cells by lentiviral infection enabling OE of Oct4 simultaneously with a puromycin (Puro) resistance gene. As expected, Oct4 transcript levels were up regulated following infection, subsequent effect was observed following Puro exposure as shown by qRT-PCR (A-B). Growing infected cells on Puro selection resulted in homogenous culture over-expressing Oct4 showing morphologic 'switch' into foci of small round cells (C).

FIGS. 9A-F are bar graphs illustrating qRT-PCR analysis of Oct4 OE HAK cells with or without exposure to VPA. OE of Oct4 induced Six2 and Osr1 but not Pax2 and Sall1. However, the combination of Oct4 OE with VPA exposure shows higher Six2 expression pattern compared to each of the single manipulations. Concomitant changes in EMT genes, down-regulation of E-cad and up-regulation of Vim, indicated that the observed morphologic 'switch' is likely to be associated with EMT (reverse embryogenesis) from which re-programming and de-differentiation may progress.

FIGS. 11A-E are bar graphs illustrating qRT-PCR analysis of particular genes following Oct4 OE at passages 5, 7 and 9.

DESCRIPTION OF EMBODIMENTS OF THE INVENTION

The present invention, in some embodiments thereof, relates to isolated populations of renal progenitor cells and methods of generating and using same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Renal failure, whether arising from an acute or chronic decline in renal function, is a severe condition that can result in substantial or complete failure of the filtration, reabsorption, endocrine and homeostatic functions of the kidney. It is therefore desirable to obtain cells such as stem cells capable of developing into cells that could supply some or all of the functions of the kidney.

The goal of renal regenerative medicine is to create an unlimited supply of human cells resembling the renal progenitors residing in the metanephric/nephrogenic mesenchyme (MM) so as be able to replenish diseased ones in renal hypoplasia/dysplasia, affording enhanced nephron development or replace glomerular podocytes by inoculating a cell population containing the podocyte progenitor cell.

In an attempt to generate such cell populations, the present inventors experimented with numerous protocols in order to dedifferentiate human adult kidney (HAK) cells.

Figure 3:
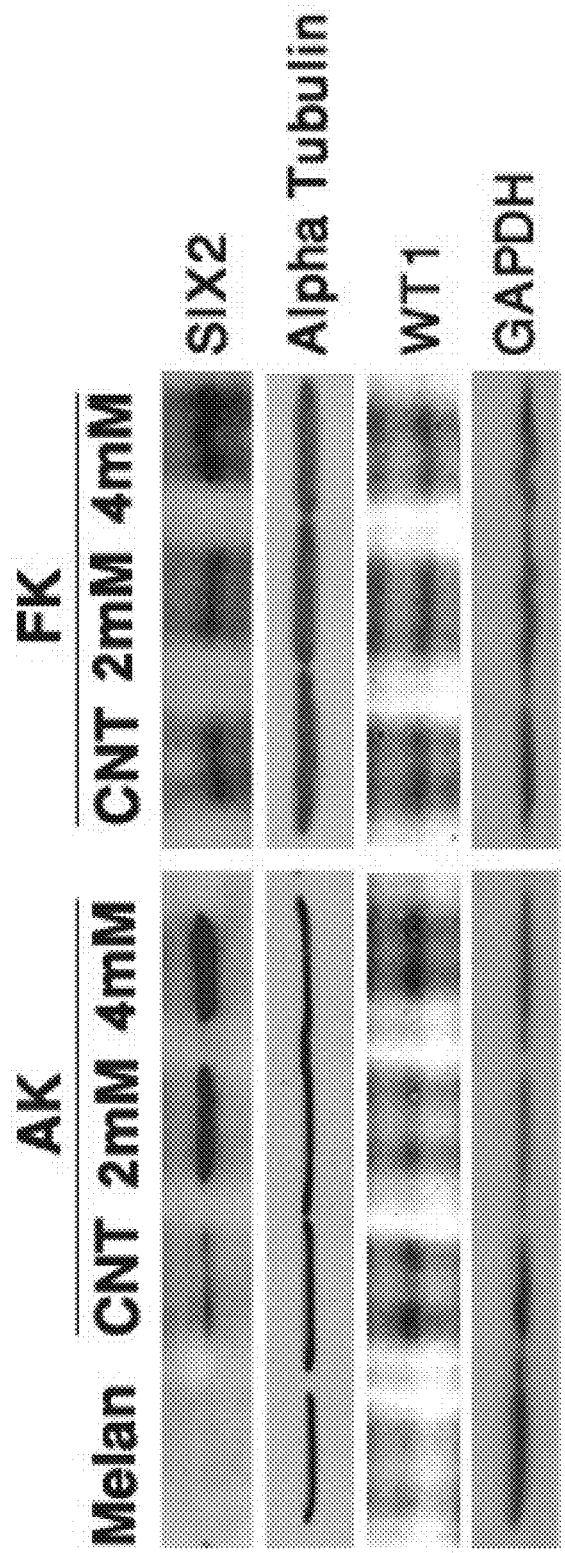
FIG. 3 is a photograph of a Western blot analysis for SIX2 and WT1 in VPA treated human adult and fetal kidney cells, showing elevated SIX2 but not WT1 protein levels in both cell types following treatment. Melanoma cells were used as negative control and alpha-tubulin and GAPDH were used for loading control.
Figure 4N:
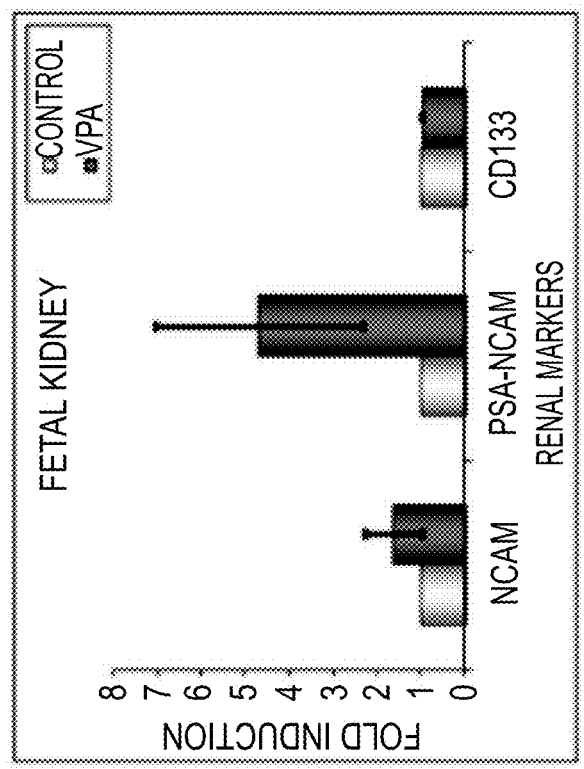
FIGS. 4A-N are graphs illustrating flow cytometric analyses of embryonic renal progenitor surface markers (NCAM, PSA-NCAM) and other markers such as CD133 in human kidney cells following treatment with 24 h −4 mM VPA. At least three independent samples of human kidneys were used. Shown are (FIGS. 4A-L) Representative FACS analysis and (FIGS. 4M-N) fold induction in expression levels demonstrating significant elevation of PSA-NCAM, NCAM and to a lesser extent of CD133.
Figure 4M:
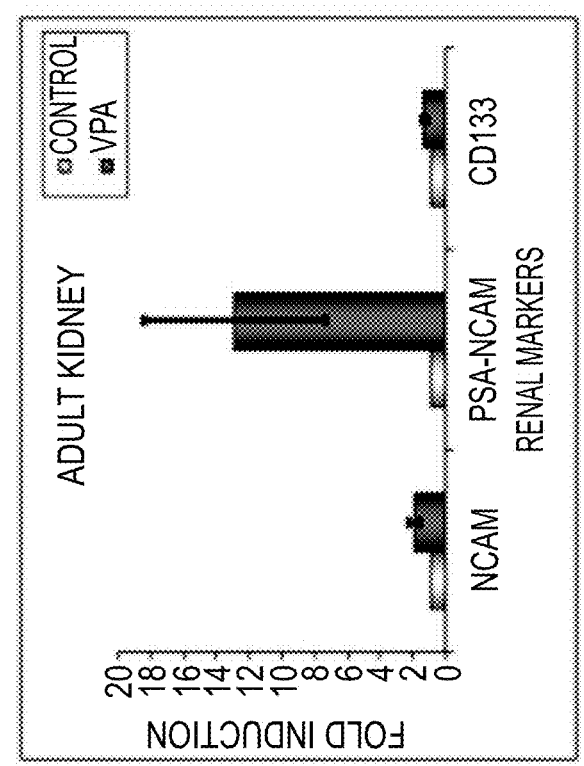

Whilst reducing the present invention to practice, the present inventors showed that epigenetic 'transcriptional' reprogramming of HAK cells via VPA or TSA/5-Aza treatment can increase the expression of pluripotency-associated genes as demonstrated by qRT-PCR analysis (FIGS. 1A-T, 2A-T and 5A-D), Western blot analysis (FIG. 3) and flow cytometry analysis (FIGS. 4A-N).

Further the present inventors surprisingly found that overexpression of a pluripotency associated gene via genetic manipulation in HAK cells did not cause the cells to fully dedifferentiate into induced pluripotent cells (iPS) (that would in turn have to be re-differentiated into the renal lineage) but rather directly induce renal progenitors, as illustrated by qRT-PCR analysis and immunohistochemistry (FIGS. 8A-C). A combination of epigenetic reprogramming using chromatin modifying agents and genetic manipulations induced a robust phenotypic switch manifested as epithelial to mesenchymal transition (EMT) simulating reverse embryogenesis in the kidney, as illustrated by qRT-PCR (FIGS. 9A-F).

Thus, according to one aspect of the present invention there is provided a method of reprogramming a differentiated renal cell towards a progenitor phenotype, the method comprising up-regulating in the differentiated renal cell an expression of at least one pluripotency associated gene and/or at least one renal stem cell associated gene, thereby reprogramming the differentiated renal cell towards a progenitor phenotype.

It will be appreciated that the differentiation status of cells is a continuous spectrum, with a terminally differentiated state at one end of this spectrum and a de-differentiated state (omnipotent state) at the other end.

Accordingly, the phrase "differentiated renal cell" as used herein, refers to a cell derived from the kidney that has progressed down the development pathway further than a progenitor cell. According to one embodiment, the differentiated renal cells comprise a specialized function and form (e.g., epithelial cells, endothelial cells, mesangial cells, vascular smooth muscle cells, and pericytes). The cells may be terminally differentiated or partially differentiated. According to an embodiment of this aspect of the present invention, the differentiated renal cells express genes associated with pluripotency (e.g. Oct4, Nanog and klf4) or genes associated with renal stem cells (e.g. any of the markers Hox11 paralogs, Osr1, Pax2, Eya1, Wt1, Sall1, Six2 and Cited1) to a lesser extent than stem cells (e.g. less than half the amount, less than one quarter of the amount and more preferably less than one tenth the amount that is expressed in stem cells).

Typically, differentiated cells are not capable of giving rise to a clone of cells.

The cells may be primary cells such as those freshly isolated from an animal (e.g. during a biopsy), or may be derived from a cell line (immortalized cells). In an exemplary aspect, the differentiated cells are mammalian cells, such as, for example, human cells or mouse cells. Differentiated cells used in the present invention may be in the form of a group or tissue.

The term "dedifferentiating" refers to any movement of the differentiation status of a cell along the spectrum toward a less differentiated state. For example, dedifferentiating includes reversing a multipotent cell back to a pluripotent cell, and reversing a terminally differentiated cell back to either a multipotent cell or a pluripotent cell. In another embodiment, dedifferentiation of a differentiated cell turns the cell back to a multipotent state.

The term "progenitor phenotype" refers to a state of a cell whereby it is committed to differentiating towards at least one type of nephron epithelia and also is capable of self-renewing. Typically, renal progenitor cells express some of the phenotypic markers that are characteristic of renal lineages. Typically, they do not produce progeny of other embryonic germ layers when cultured by themselves in vitro, unless dedifferentiated or reprogrammed. It will be appreciated that it is not implied that each of the cells within the population have the capacity of forming more than one type of progeny, although individual cells that are multipotent renal progenitor cells may be present.

According to one embodiment of this aspect of the present invention, the renal progenitor cells of the present invention express Six2 and/or Osr1. According to yet another embodiment of this aspect of the present invention, the renal progenitor cells of the present invention express Six2, Osr1, Pax2 and vimentin. According to yet another embodiment of this aspect of the present invention, the renal progenitor cells of the present invention do not express e-cadherin. According to yet another embodiment of this aspect of the present invention, the renal progenitor cells of the present invention are capable of giving rise to a clone of cells.

As mentioned, the method of the present invention is effected by up-regulating in the differentiated renal cell an expression of at least one pluripotency associated gene and/or at least one renal stem cell associated gene.

As used herein, the phrase "pluripotency associated gene" refers to a gene which is upregulated at least two fold, more preferably at least 5 fold in a pluripotent cell as compared to a non-pluripotent cell.

Examples of pluripotent associated genes include those that belong to the Oct family, the Sox family, klf family, Myc family, Lin family and Nanog (mouse NM_028016 and human NM_024865).

Examples of genes belonging to the Oct family include, for example, Oct3/4 (NM_013633, mouse and NM_002701, human), Oct1A (NM_198934, mouse and NM_002697, human), Oct6 (NM_011141, mouse and NM_002699, human), and the like. Oct3/4 is a transcription factor belonging to the POU family, and is reported as a marker of undifferentiated cells (Okamoto et al., Cell 60:461-72, 1990). Oct3/4 is also reported to participate in the maintenance of pluripotency (Nichols et al., Cell 95:379-91, 1998).

Examples of genes belonging to the Sox (SRY-box containing) family include, for example Sox1 (NM_009233, mouse and NM_005986, human), Sox3 (NM_009237, mouse and NM_005634, human), Sox7 (NM_011446, mouse and NM_031439, human), Sox15 (NM_009235, mouse and NM_006942, human), Sox17 (NM_011441, mouse and NM_022454, human) and Sox18 (NM_009236, mouse and NM_018419, human), and a preferred example includes Sox2 (NM_011443, mouse and NM_003106, human).

Examples of genes belonging to the klf (Knippel-like factor) family include, for example Klf1(NM_010635, mouse and NM_006563, human), Klf2 (NM_008452, mouse and NM_016270, human), Klf4 (NM_010637, mouse and NM_004235, human) and Klf5 (NM_009769, mouse and NM_001730, human).

Examples of genes belonging to the Myc (myeolcytomatosis oncogene) family include, for example C-Myc (NM_010849, mouse and NM_002467, human), N-Myc (NM_008709, mouse and NM_005378, human) and L-Myc (NM_008506, mouse and NM_005376, human).

Examples of genes belonging to the Lin (myeolcytomatosis oncogene) family include, for example Lin28b (NM_001031772, mouse and NM_001004317, human).

The phrase "renal stem cell associated gene" refers to a gene that is upregulated at least 2 fold and more preferably at least 5 fold in a renal stem cell compared with a differentiated renal cell.

Examples of renal stem cell associated genes include, but are not limited to six2 (NM_016932-accession number: AF136939), osr1 (NM_145260.2), pax2 (NM_003987.3, NM_000278.3, NM_003988.3, NM_003989.3, NM_003990.3) sall1 (NM_002968) and cited 1 (NM_001144885.1, NM_001144886.1, NM_001144887.1 NM_004143.3).

It will be appreciated that the present invention contemplates up-regulation of any combination of the above mentioned genes and any number of the above mentioned genes.

According to one embodiment osr1 and six2 are upregulated.

According to yet another embodiment six2 and pax2 are up-regulated.

According to still another embodiment six2 and sall1 are up-regulated.

According to yet another embodiment, pax2 and sall1 are up-regulated.

According to still another embodiment osr1, six2 and pax2 are up-regulated.

Various methods are contemplated in order to up-regulate expression of the above described genes.

According to one embodiment up-regulation is effected by contacting the cells with at least one chromatin modifying agent.

According to one embodiment, the chromatin modifying agent of the present invention is a histone deacetylase inhibitor.

Examples of chromatin modifying agents include, but are not limited to TSA, sodium butyrate, 5-aza-2'-deoxycytidine, valproic acid, vorinostat, LBH-589, apicidin, TPX-HA analogue, CI-994, MS-275, MGCD0103, and derivatives or analogues of the above-mentioned. Further examples of chromatin modifying agents are provided in U.S. Patent Application No. 20090275032, incorporated herein by reference.

According to one embodiment, the differentiated cells of the present invention are dedifferentiated in a culture medium containing the chromatin modifying agent for at least 24 hours. Preferably, the chromatin modifying agent is present in the culture medium during the entire propagation phase.

Figure 7A:
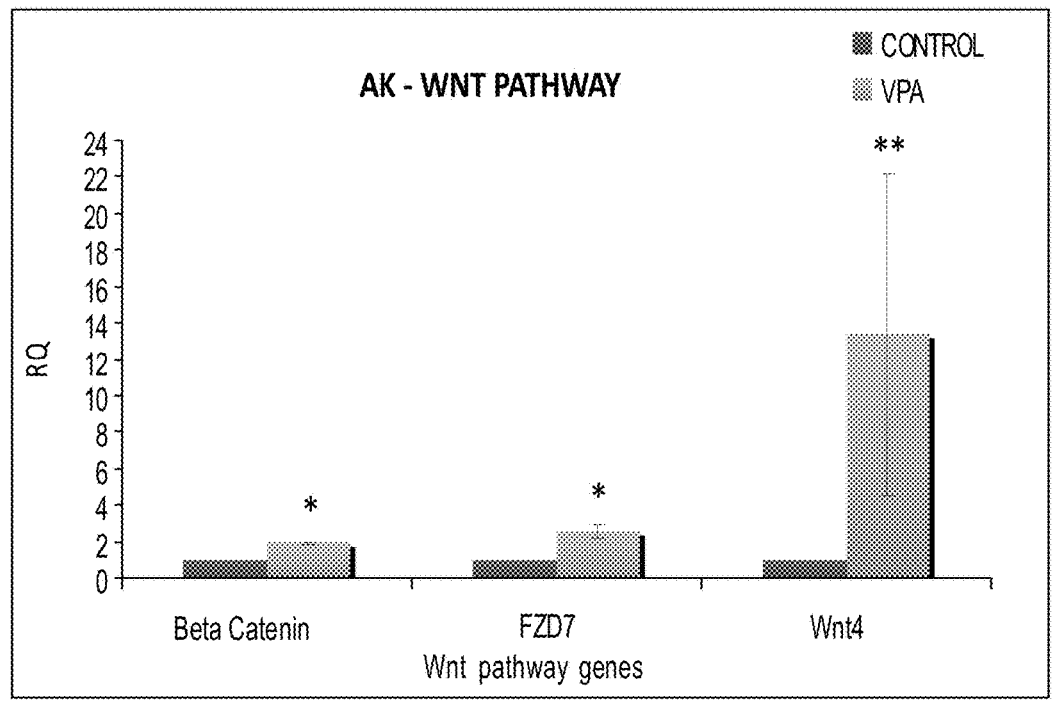
FIGS. 7A-B are bar graphs illustrating qRT-PCR analysis of the Wnt pathway genes, Wnt4, frizzled? (FZD7) and β-catenin human adult and fetal kidney cells subjected to VPA. Data were calculated as average±SD. *, p<0.05; **, p<0.05 after logarithmic transformation versus untreated controls.
Figure 7B:
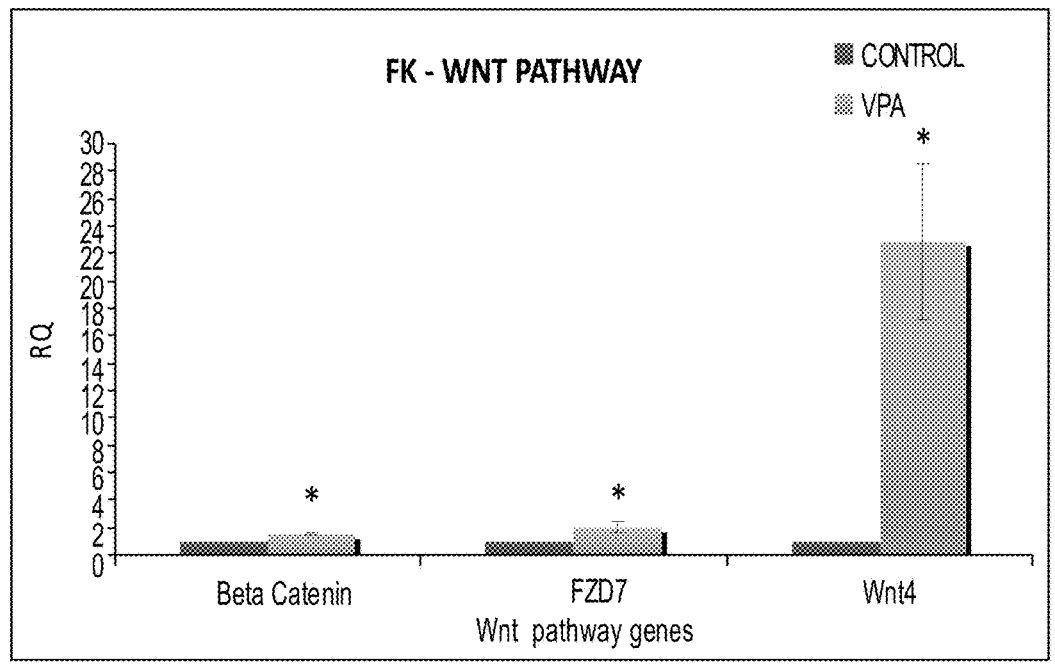
Figure 7N:
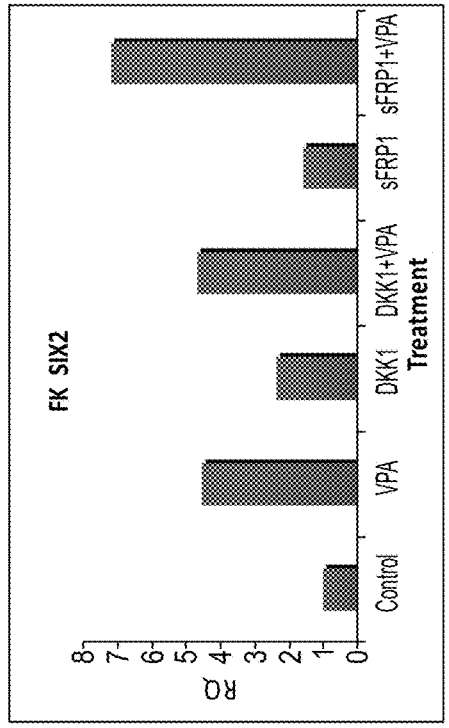
FIGS. 7N-Q are bar graphs illustrating quantitative reverse transcription-polymerase chain reaction analysis of Six2 and Osr1 following the addition of Wnt pathway antagonists, DKK1 and sFRP1 to non-treated and VPA treated human and fetal kidney cells. Representative experiment of three yielding similar results.
Figure 7O:
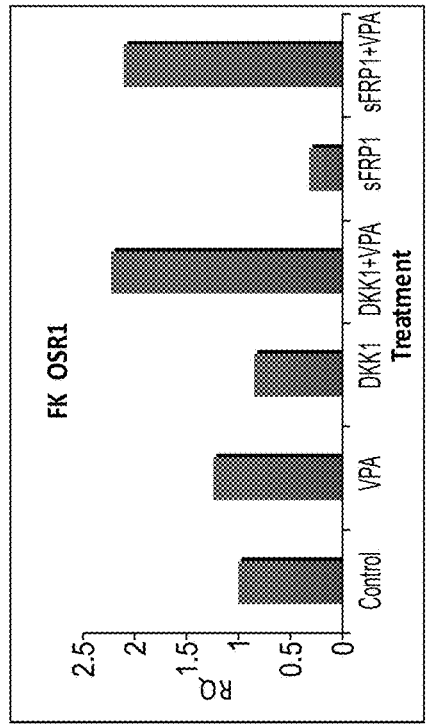
Figure 7P:
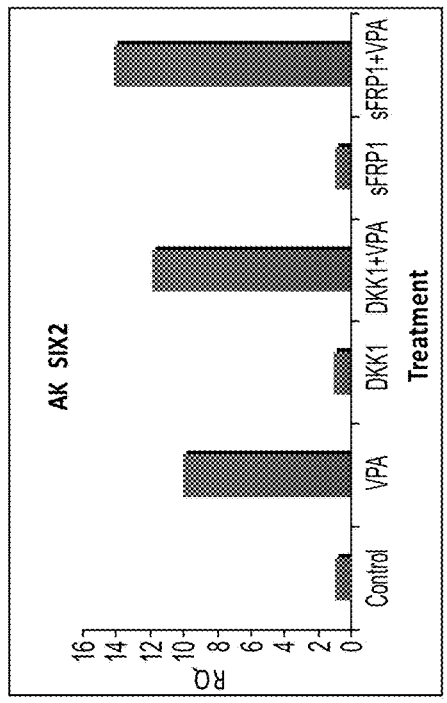
Figure 7Q:
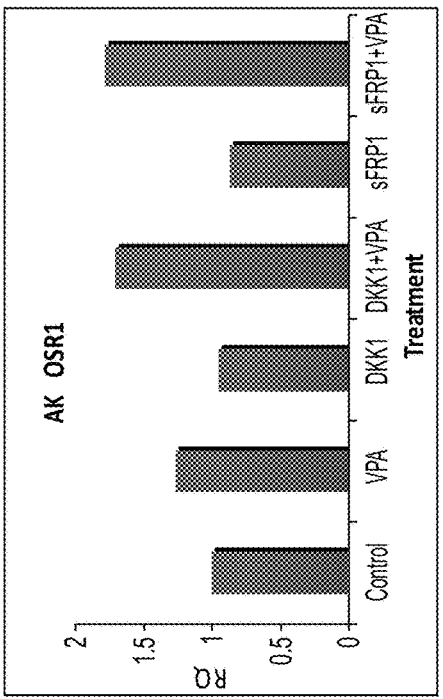
Figure 7R:
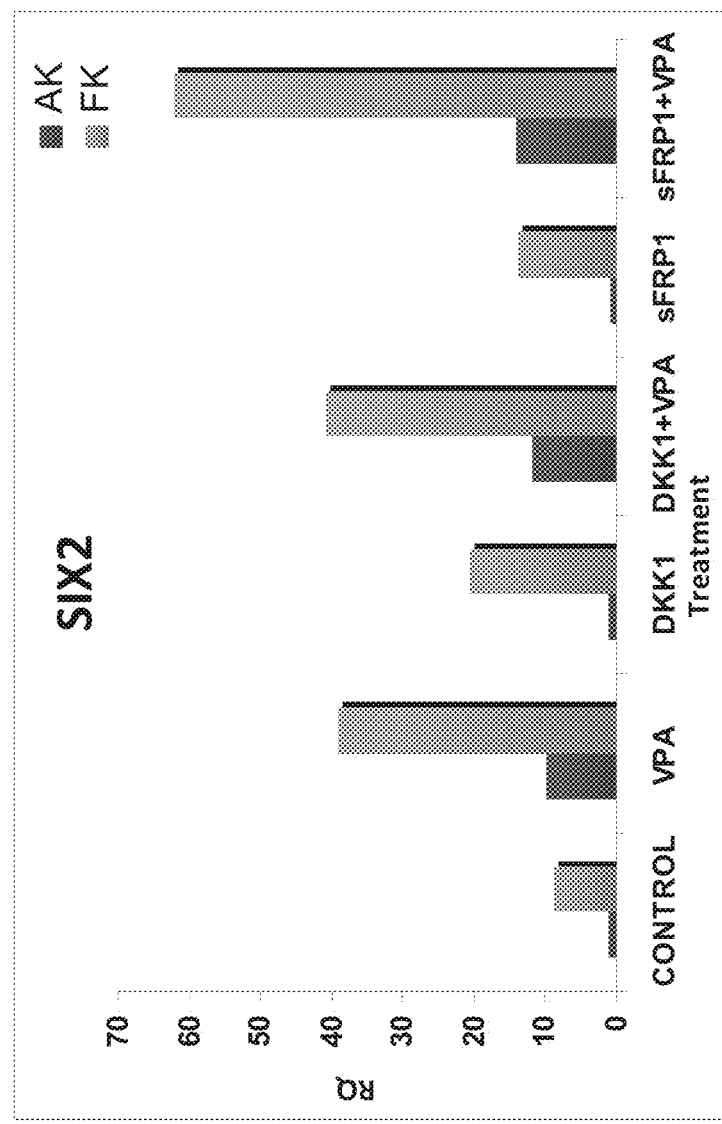
FIG. 7R is a bar graph illustrating qRT-PCR analysis of Six2 expression, in human adult and fetal kidney cells following the addition of Wnt pathway antagonists, DKK1 and sFRP1 to non-treated and VPA treated human and fetal kidney cells. A comparison in Six2 levels between the various treatment groups of adult and fetal kidney cells showed, as expected, higher Six2 in HFK cells, combined VPA/Wnt inhibitor treatment of HAK cells resulted in Six2 re-induction to similar and even higher levels to those of control developing human kidney cells
Figures 10A, 10B, 10C, 10D, 10E, 10F:
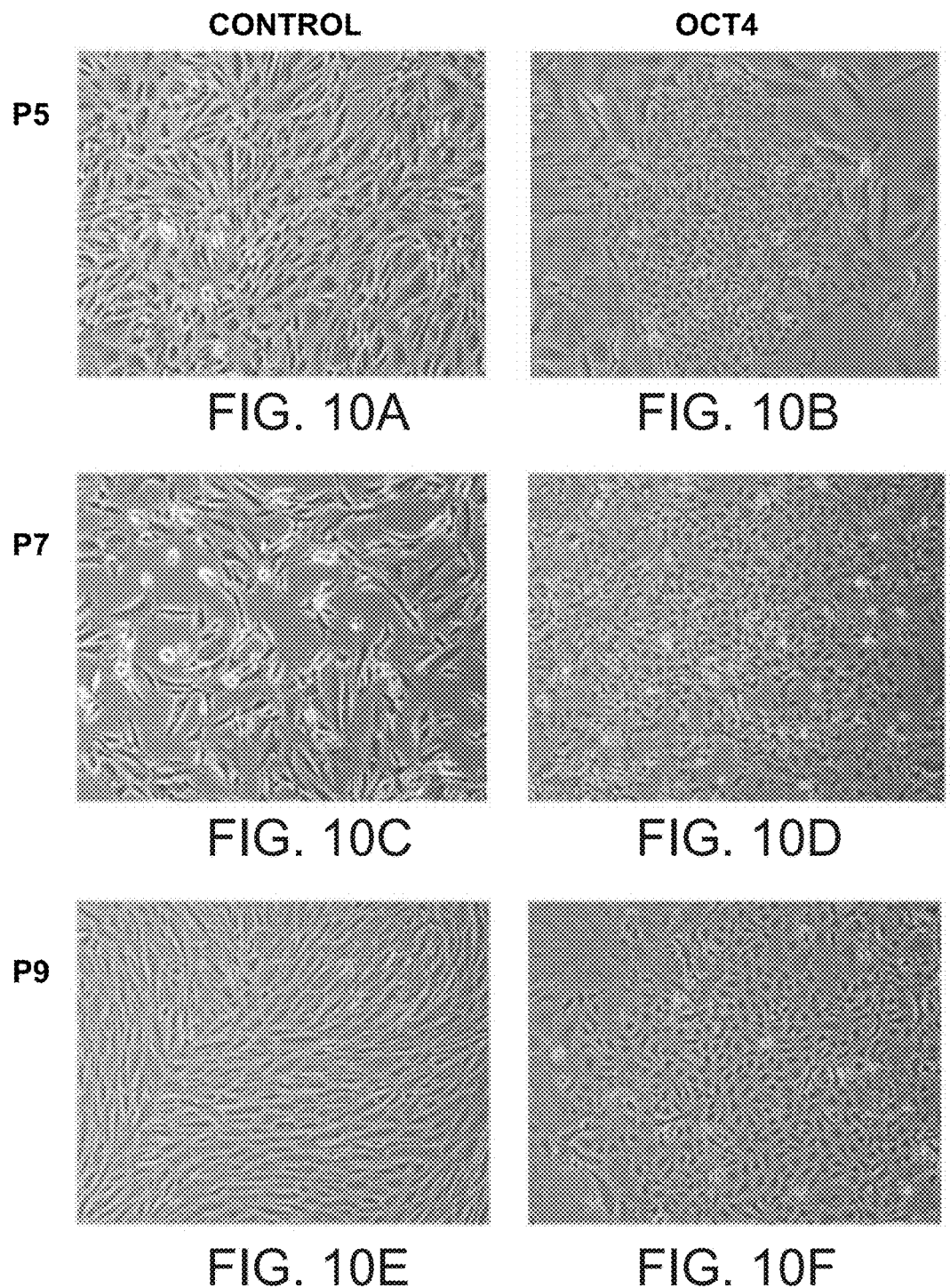
FIGS. 10A-F are photographs illustrating the morphology of HAK following Oct4 OE at passages 5, 7 and 9.

The present inventors have shown that if a Wnt antagonist is used in combination with a chromatin modifying agent, a synergistic effect is seen whereby the upregulation of renal stem cell specific genes in the cells is even more apparent (FIGS. 7A-R). Thus, the present invention conceives of addition of Wnt antagonists (e.g. DKK1 and sFRP1) to the culture medium in combination with the chromatin modifying agents. The present invention also contemplates other Wnt antagonists such as siRNAs, RNAzymes, DNAzymes, miRNAs and the like. Such wnt antagonists are typically transfected into the cells as described herein below.

Another method contemplated by the present inventors in order to up-regulate expression of the genes mentioned above is by genetic manipulation. This may be effected in combination with (concomitantly with, prior to or following) chromatin modifying agents or instead of chromatin modifying agents.

The genes are typically introduced into the cell in the form of a vector, i.e., a nucleic acid molecule capable of transporting another nucleic acid to which it has been linked. The vector can be a viral vector (e.g., replication defective retroviruses, adenoviruses and adeno-associated vectors), wherein additional DNA segments can be ligated into the viral genome. Certain vectors are capable of autonomous replication in a host cell into which they are introduced. Other vectors (e.g., non-episomal mammalian vectors) are integrated into the genome of a host cell upon introduction into the host cell, and thereby are replicated along with the host genome. Expression vectors are capable of directing the expression of genes to which they are operably linked.

The recombinant expression vectors that can be introduced into renal stem cells include one or more regulatory sequences that are operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the cell in which the gene is to be expressed, the level of expression of protein desired, etc.

Vector DNA can be introduced into cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those that confer resistance to drugs, such as G418, hygromycin and methotrexate. Nucleic acid encoding a selectable marker can be introduced into a host cell on the same vector as that encoding the transgene or can be introduced on a separate vector. Cells stably transfected with the introduced nucleic acid can be identified by drug selection (e.g., cells that have incorporated the selectable marker gene will survive, while the other cells die).

It will be appreciated that the cells of the present invention may be transfected with additional genes in order to confer additional properties upon them. This may be effected concomitantly with transfection of the pluripotency associated genes and/or renal stem cell associated genes or following same. For example, genes encoding erythropoeitin or insulin can be introduced into the cells of the present invention. For treatment of anemia associated with renal failure or diabetes it can be useful to introduce into a patient a stem cells modified to express erythropoeitin or insulin. The renal stem cells can be stably or transiently transfected with DNA encoding any therapeutically useful polypeptide.

The renal cells of the invention can also be provided with a transgene encoding VEGF or some other factor that can promote growth and or differentiation of cells.

Other candidate genes for gene therapy include, for example, genes encoding the alpha 5 chain of type IV collagen (COL4A5), polycystin, alpha-galactosidase A, thiazide-sensitive sodium chloride cotransporter (NCCT), nephrin, actinin, or aquaporin 2.

Following the dedifferentiation procedure, renal progenitor cells may be isolated. According to one embodiment, the renal progenitor cells are isolated by flow cytometry using antibodies against proteins that are preferentially expressed in renal progenitor cells and a fluorescence-activated cell sorter (FACS). Co-filed PCT Application Agent References, 48270, filed on 25 Feb. 2010, which claims the benefit under 119(e) of U.S. Provisional Patent Application No. 61/202, 425 filed 26 Feb. 2009 to the present inventors, incorporated herein by reference teaches a variety of markers that can be used for this analysis including for example NCAM and ALDH/ALDH$^{bright}$.

As used herein, the term "flow cytometry" refers to an assay in which the proportion of a material (e.g. renal cells comprising a particular maker) in a sample is determined by labeling the material (e.g., by binding a labeled antibody to the material), causing a fluid stream containing the material to pass through a beam of light, separating the light emitted from the sample into constituent wavelengths by a series of filters and minors, and detecting the light.

A multitude of flow cytometers are commercially available including for e.g. Becton Dickinson FACScan and FACScalibur (BD Biosciences, Mountain View, Calif.). Antibodies that may be used for FACS analysis are taught in Schlossman S, Boumell L, et al, [Leucocyte Typing V. New York: Oxford University Press; 1995] and are widely commercially available.

Once isolated, cells of the present invention may be cultured and allowed to proliferate. According to one embodiment the cells are maintained in serum free medium. According to another embodiment the cells are allowed to proliferate in serum containing medium. Optionally the cells may then be directed to differentiate into a desired lineage.

The developmental potential of progenitor cells thus obtained can be investigated using methods which are well known in the art. For example by injection into other organs (liver, muscle, heart and bone marrow) to test their multipotency Clarke et al. describes protocols for investigating the development potential of stem cells (Clarke et al. 2000 Science 288:1660).

Methods of analyzing the differentiation status of the dedifferentiated cells of the present invention is by analyzing the expression levels of particular genes—e.g. those associated with a differentiated state, those associated with a pluripotent state and/or those associated with a progenitor state.

Methods which can be used to analyze expression levels of genes include for example qRT-PCR, Northern blot analysis, Western blot analysis, immunohistochemistry.

The renal progenitor cells of the invention can be used to supplement or substitute for kidney cells that have been destroyed or have reduced function. Thus, they can be used to treat patients having poor or no kidney function. The renal stem cells of the invention or cells derived from the renal stem cells of the invention may be capable of performing the filtration and reabsorptive/secretive functions of the kidney.

Thus according to an aspect of the present invention there is provided a method of treating a renal damage in a subject in need thereof comprising administering to the damaged kidney of the subject a therapeutically effective amount of any of the isolated population of cells, thereby treating the renal disease in the subject.

Cells of the present invention can be used to treat any form of acute or chronic kidney disease, diabetic nephropathy, renal disease associated with hypertension, hypertensive acute tubular injury (ischemic, toxic), interstitial nephritis, congenital anomalies (Aplasia/dysplasia/obstructive uropathy/reflux nephropathy); hereditary conditions (Juvenile nephronophtisis, ARPCKD, Alport, Cystinosis, Primary Hyperoxaluria); Glomerulonephritides (Focal Segmental Glomerulosclerosis); Multisystem Diseases (SLE, HSP, HUS).

The cells may be administered per se or as part of a pharmaceutical composition where they are mixed with a suitable carrier or excipient. As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the renal progenitor cells (or cells differentiated therefrom) accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

The renal progenitor cells or cells derived from the renal progenitors cells can be administered into a subject such as surgically or by infusion. For example, renal progenitor cells are injected in vivo into the blood stream or directly into a kidney that is in the postischemic recovery phase. This can be tested easily in an animal model predictive of ischemic kidney damage, the renal pedicle of an anesthetized mouse is clamped for 30 minutes to induce kidney ischemia. Renal progenitor cells are then injected into the juxtamedullary region (approximately 2000 cells at a depth of 2-4 mm). After 2 weeks of recovery, immunohistochemical analysis is used as described above to look for differentiated cells surface markers GP330, Tamm-Horfall, Dolichos Biflorous, and the like. Post-incorporation differentiation status can then be compared to pre-injection marker status.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

The number of transplanted cells and intervals between transplantations may be adjusted individually to provide a sufficient biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, transplantations can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

The progenitor cells of the invention or cells derived from the stem cells of the invention (e.g., epithelial cells endothelial cells, mesangial cells, vascular smooth muscle cells, and pericytes) can be used to construct artificial kidney systems. Such a system can be based on a hollow fiber filtration system.

In one example of a filtration device, the progenitor cells of the invention or differentiated progeny thereof are grown on the interior of hollow fibers having relatively high hydraulic conductivity (i.e., ultrafiltration coefficient). The hollow fiber passes through a chamber that is provided with a filtrate outlet port. Arterial blood containing metabolic waste and other unwanted material is introduced into one end of the hollow fiber through an inlet port. Blood passed through the fiber and exits the other end of the fiber through an outlet port where it passed into the patient's vascular venous flow. As blood passes through the fiber, filtrate pass through the cells lining the interior of the fiber and through the hollow fiber itself. This filtrate then passes out of the chamber containing the fiber through the filtrate outlet port. The device preferably includes many such hollow fibers each of which can be in its own chamber. Alternatively many, many hollow fibers (100-100,000 or even more) can be bundled together in a single chamber.

The cells of the invention can be used to create a tubule-processing device. In such a device the stem cells of the invention or differentiated cells derived from the stem cells of the invention can be grown in a layer on the exterior of the semipermeable hollow fiber. The fiber is placed in a chamber that is provided with an inlet port and an outlet port. As ultrafiltrate from filtered blood flows through the chamber, reabsorbant passes through the cell layer and through the wall of the fiber into the lumen of the fiber from which it can be directed back into the patient's systemic circulation. Ultrafiltrate that is not reabsorbed passes through the outlet port of the chamber.

In the devices described above, it can be desirable to coat the fiber surface that will bear the cell layer with extracellular matrix components. For example, the fiber can be coated with materials such as collagen (e.g., Type I collagen or Type IV collagen), proteoglycan, fibronectin, and laminin or combinations thereof. It can be desirable to combine various cell types on the inner or outer surface of the fibers. For example, it can be desirable to include endothelial cells and pericyte, vascular smooth muscle cells or mesangial cells or fibroblasts or combinations thereof. It can also be useful to provide a feeder layer of cells, e.g., irradiated fibroblasts or other cells that can provide soluble factors and structural support to cells they are indirectly or directly in contact with.

The above-described filtration system and the above-described tubule processing system can be combined to create an artificial kidney. Such systems are described in U.S. Pat. No. 6,150,164, hereby incorporated by reference. A number of suitable materials for forming the hollow fiber are described in U.S. Pat. No. 6,150,164, hereby incorporated by reference.

The present invention provides a method of using the progenitor cells of the present invention to characterize cellular responses to biologic or pharmacologic agents involving isolating the cells as described, expanding the cells to establish a plurality of progenitors, contacting the progenitor cultures with one or more biologic or pharmacologic agents, identifying one or more cellular responses to the one or more biologic or pharmacologic agents, and comparing the one or more cellular responses of the cultures. Tissue culture techniques known to those of skill in the art allow mass culture of hundreds of thousands of cell samples from different individuals, providing an opportunity to perform rapid screening of compounds suspected to be, for example, teratogenic or mutagenic.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

GENERAL MATERIALS AND METHODS

Tissue Samples: human tissues samples were collected according to the Helsinki requirements. Human fetal kidney cells (HFK) were collected from elective abortions at fetal gestational age ranged from 15 to 19 weeks. Normal human adult kidney cell (HAK) samples were retrieved from borders of RCC tumors from partial nephrectomy patients.

Establishment of Primary Cultures from Human Kidney Tissues: Collected tissues were minced in HBSS, soaked in IMDM Medium (Invitrogen) supplemented with 0.1% collagenase II (Invitrogen). The digested tissue was then gradually forced through a 100 μm, 70 μm and 50 μm cell strainer to achieve a single cell suspension, and cultured in growth medium supplemented with FBS 10%, L-Glutamin 1%, Pen-Strep 1% and growth factors: 50 ng/ml of bFGF, 50 ng/ml of EGF and 5 ng/ml of SCF (R&D systems).

Cell Treatment: Cells were treated for 24 hours with growth medium supplemented with 1, 2, or 4 mM VPA (Sigma) or with $H_2O$ for control sample. Otherwise, cells were treated for 24 hours with growth medium supplemented with the combination of 75 μM TSA (Sigma) and 250 μM 5-AZA (Sigma) or with 100% Ethanol and Acetic Acid (Acetic Acid: $H_2O$ 1:1) for control sample. In some experiments Wnt pathway inhibitors were used in conjunction with VPA as following: cells were treated for 72 hours with growth medium supplemented with 3 μg/ml DKK1 (R&D systems) or with 7 μg/ml sFRP1 (R&D systems). 24 hours prior to harvesting VPA at a concentration of 4 mM was added to the cell culture.

Flow Cytometry: Cells were detached from culture plated with non-enzymatic cell dissociation solution (Sigma-Aldrich). Cells ($1 \times 10^5$ in each reaction) were suspended in 50 μl of FACS buffer [0.5% BSA and 0.02% sodium azid in PBS (Sigma-Aldrich and Invitrogen, respectively)] and blocked with FcR Blocking Reagent (MiltenyiBiotec) and human serum (1:1) for 15 minutes. Cells were then incubated for 45 minutes with the following primary antibodies: CD24-PE, NCAM1-PE, (both from eBioscience), CD133-APC, PSA-NCAM (both from MiltenyiBiotec), FZD7-biotin, NTRK2 (both from R&D Systems) or a matching isotype control. Cells were washed with FACS buffer, and incubated for 30 minutes with a secondary antibody if needed: goat anti mouse Streptavidin-APC (BD) or goat anti mouse Alexa Fluor 647 (Invitrogen). Cell's labeling was detected using FACSCalibur (BD). Flow cytometry results were analyzed using FlowJo analysis software. Viable cells were gated by both their FSC/SSC profile and 7AAD (eBioscience) exclusion.

Quantitative Reverse Transcription-PCR: Total RNA from kidney tissue cultured cells was isolated using the TRIZOL reagent (Invitrogen) according to the manufacturer's protocols. cDNA synthesis was carried out using Verso kit (Thermo scientific) with Random primers. Quantitative RT PCR was performed using an ABI7900HT sequence detection system (Perkin-Elmer/Applied Biosystems) in the presence of SYBR green (SYBR green PCR kit; Qiagen). The sequences of the specific primers used for PCR are summarized in Table 1. Each analysis reaction was performed in duplicates or triplicates. GapDH was used as an endogenous control throughout all experimental analyses. Analysis was performed using the $-\Delta\Delta Ct$ method, which determines fold changes in gene expression relative to a comparator sample.

TABLE 1

| Gene | Sequence |
|---|---|
| SIX2 | 5'-CCA AGG AAA GGG AGA ACA ACG-3'-SEQ ID NO: 1<br>5'-GCT GGA TGA TGA GTG GTC TGG-3'-SEQ ID NO: 2 |
| WT1 | 5'-GCT GTC CCA CTT ACA GAT GCA-3'-SEQ ID NO: 3<br>5'-TCA AAG CGC CAG CTG GAG TTT-3'-SEQ ID NO: 4 |
| PAX2 | 5'-CCC AGC GTC TCT TCC ATC A-3'-SEQ ID NO: 5<br>5'-GGC GTT GGG TGG AAA GG-3'-SEQ ID NO: 6 |
| OSR1 | 5'-TGT ATG GTT TCA GCG CGT TG-3'-SEQ ID NO: 7<br>5'-GGG TTG AAT GAC ATG AGG GAA-3'-SEQ ID NO: 8 |
| SALL1 | 5'-CAA TCT TAA GGT ACA CAT GGG CAC-3'-SEQ ID NO: 9<br>5'-TGC CTC CTA GAA ATG TCA TGG G-3'-SEQ ID NO: 10 |
| E-CADHERIN | 5'-AGT GCC AAC TGG ACC ATT CA-3'-SEQ ID NO: 11<br>5'-TCT TTG ACC ACC GCT CTC CT-3'-SEQ ID NO: 12 |
| VIMENTIN | 5'-ACA CCC TGC AAT CTT TCA GAC A-3'-SEQ ID NO: 13<br>5'-GAT TCC ACT TTG CGT TCA AGG T-3'-SEQ ID NO: 14 |
| OCT4 | 5'-GAG AAC CGA GTG AGA GGC AAC C-3'-SEQ ID NO: 15<br>5'-CAT AGT CGC TGC TTG ATC GCT TG-3'-SEQ ID NO: 16 |
| NANOG | 5'-AAT ACC TCA GCC TCC AGC AGA TG-3'-SEQ ID NO: 17<br>5'-TGC GTC ACA CCA TTG CTA TTC TTC-3'-SEQ ID NO: 18<br>5'-ACC AGG CAC TAC CGT AAA CAC A-3'-SEQ ID NO: 19 |
| KLF4 | 5'-GGT CCG ACC TGG AAA ATG CT-3'-SEQ ID NO: 20<br>5'-ACC AGG CAC TAC CGT AAA CAC A-3'-SEQ ID NO: 39 |
| GAPDH | 5'-TCCACCACCCTGTTGCTGTA-3'-SEQ ID NO: 40<br>5'-TCCACCACCCTGTTGCTGTA-3'-SEQ ID NO: 41 |

Chromatin Immunoprecipitation Assay (ChIP): 10×10⁶ cells adult kidney cells were grown. Untreated cells (control) or cells treated with VPA (4 mM) were cross-linked with 1% formaldehayde for 10 min at RT in culture medium. The cells were washed and harvested in cold phosphate-buffered saline (PBS) containing protease inhibitors (Complete mini, Roche Applied Science) and Pepstatin (Sigma). The cells were then washed with Buffer B (20 mM Hepes pH 7.6, 0.25% Triton-x, 10 mM EDTA, 0.5 mM EGTA) and Buffer C (50 mM Hepes pH 7.6, 150 mM NaCl, 1 mM EDTA, 0.5 mM EGTA) were resuspended in 300 µl of SDS lysis buffer [1% SDS, 10 mM EDTA and 50 mM Tris-HCl (pH 8.1)], and incubated on ice for 10 minutes. Lysates were sonicated with 8×10 second bursts and debris were removed by centrifugation for 10 minutes at 1000 g, at 4° C. Supernatants were diluted 10-fold in ChIP dilution buffer [0.01% SDS, 1.1% Triton X-100, 1.2 mM EDTA, 16.7 mM Tris-HCl (pH 8.1) and 167 mM NaCl] and pre-cleared by incubating with 40 µl of protein A+salmon sperm beads (Upstate Biotechnology) for 30 minutes at 4° C. Beads were pelleted for 1 minute at 1000 g at 4° C. A total of 10 µl of the supernatant was saved as input, and the rest was divided into equal aliquots and incubated by rocking with either control Ab (IgG) or with of specific antibodies; Trimethyl-Histon 3K27 antibody (Upstate Biotechnology), anti acetylatedhistone H4 (Upstate Biotechnology) over night at 4° C. A total of 60 µl of protein A+salmon sperm beads was added, and the samples were rocked for 2 hours at 4° C. The complexes on the beads were washed for 5 minutes at 4° C. with the following buffers: low salt [0.1% SDS, 1% Triton X-100, 2 mM EDTA, 20 mM Tris-HCl (pH 8.1) and 150 mM NaCl], high salt [0.1% SDS, 1% Triton X-100, 2 mM EDTA, 20 mM Tris-HCl (pH 8.1), 500 mM NaCl], LiCl wash [0.25 M LiCl, 1% Nonidet P-40, 1% deoxycholate, 1 mM EDTA and 10 mM Tris-HCl (pH 8.1)], and twice with TE [10 mM Tris-HCl and 1 mM EDTA (pH 8.0)]. Immune complexes were eluted twice with 200 µl of elution buffer [1% SDS and 0.1 M NaHCO₃]for 15 minutes at room temperature. The samples were de-cross-linked by adding 16 µl of 5 M NaCl, 8 µl of 0.5 M EDTA (pH 6.5) and 16 µl of 1M Tris-HCl (pH 8.1) and incubated O.N at 65° C. Proteinase K (10 mg/ml) and the samples were incubated for additional 2 hours at 55° C. Immunoprecipitated DNA was recovered by phenol/chloroform extraction and ethanol precipitation and was analyzed by quantitative RT PCR. Primer sets of Six2, WT1, and GapDH promoters are summarized in Table 2, herein below.

Methylation Depletion Immunoprecipitation (MeDIP): 10 µg of sonicated genomic DNA (100-400 bp in length) was denatured, incubated O/N at 4° C. with 10 µg/µl of anti-methyl cytosine antibody (Diagenode, Belgium), and subsequently with 60 µl of protein A fast flow beads (Upstate Biotechnologies) for 2 hours at 4° C. The beads were washed and incubated with digestion buffer (50 mM Tris-HCl pH 8.0, 10 mM EDTA, 0.5% SDS) and proteinase K for 3 hours and the DNA extracted by phenol-chloroform and EtOH precipitation. The samples were tested by quantitative RT PCR with the indicated primers at table 2. The sonicated DNA served as input.

TABLE 2

| Primer | Sequence |
|---|---|
| six2 CpG-1157 | 5'-AAGCAAAAAACAGGACCCCC-3'-SEQ ID NO: 21<br>5'-AACGGAGGCAAGATTCCCA-3'-SEQ ID NO: 22 |
| six2 CpG-955 | 5'-GAAGCCCCACCACCGTCCTAGA-3'-SEQ ID NO: 23<br>5'-ACTTAACCCCACGGGTCCCACA-3'-SEQ ID NO: 24 |
| six2 CpG-731 | 5'-GAAGTCGATTCTCCGGCGT-3'-SEQ ID NO: 25<br>5'-CCCACCCCCATCCTAGAA AC-3'-SEQ ID NO: 26 |
| six2 CpG-541 | 5'-GGGTAGAATGTGCCCGGTGAACAGA-3'-SEQ ID NO: 27<br>5'-AGGGAAGGCGGAGACCGTTTAAGG-3'-SEQ ID NO: 28 |
| six2 CpG-412 | 5'-GCTGCCCAAACTTTCTTCCCCTG-3'-SEQ ID NO: 29<br>5'-CGAAAAGGGGTGGATCGAGGTG-3'-SEQ ID NO: 30 |
| six2 CpG-92 | 5'-CGAGGCTCGGGTTACCAGT-3' SEQ ID NO: 31<br>5'-CCCTGATTGGTCCGGTTATCT-3' SEQ ID NO: 32 |
| WT1 CpG | 5'-GCGGCGCTCGAGAAGTTAT-3' SEQ ID NO: 33<br>5'-GGTCTCAGAACCGAGTGGGAG-3' SEQ ID NO: 34 |
| GapDH | 5'-TCGACAGTCAGCCGCATCT-3' SEQ ID NO: 35<br>5'-CTAGCCTCCCGGGTTTCTCT-3' SEQ ID NO: 36 |
| D4Z4 1168 | 5'-TCGCTCTGGTCTTCTACGTGG-3' SEQ ID NO: 37<br>5'-AGTCTTGAGTGTGCCAGGCC-3' SEQ ID NO: 38 |

Western Blot: AK, FK (treated and untreated) and Melanoma cells were harvested with Tripsin/EDTA. Cell extracts were prepared with lysis buffer (50 mM Tris-HCl, 150 mM NaCl, 0.1 mM EDTA, 0.5 mM DTT, 1.5 mM MgCl, 0.5% Triton-X) and their concentrations were detected by BCA protein assay kit (Thermo scientific). 100 μg of total proteins were heated at 95° C. for 5 min with laemmli sample buffer (Bio-rad) and then were loaded on SDS-10% polyacrylamide gel. After electrophoresis, proteins were transferred to nitrocellulose membrane that was blocked with 5% nonfat dry milk overnight at 4° C. The membrane was reacted with the required antibodies, namely Six2 (Affinity Bioreagents), WT1 (Santa Cruz), goat anti-rabbit IgG (Jackson). The membrane was reacted with ECL substrate (Thermo scientific) and was exposed to medical x-ray film (Fuji).

Immunofluorescence Staining: AK, FK (treated and untreated) human epithelial cell line and fibroblast cell line were fixed with acetone at −20° C. for seven minutes and washed with PBS. Cells were blocked with 7% human serum in PBS for 15 minutes followed by incubation with β-catenin antibody (1:150) (Chemicon international) for 60 minutes. Cells were washed and then incubated with secondary antibody with Cy-3 conjugated anti-mouse IgG (1:200) (Jackson) for 30 minutes. For nuclear staining, cells were washed with PBS containing Hochest (Dako). The presence of β-catenin was examined under a Zeiss confocal fluorescence microscope.

Creation of Oct4 OE Culture by Lentivital Infection: 293T cells were co-transfected by calcium phosphate with pSin-EF2-Oct4-Pur vector (Addgene, Yu J et al. Science. 2007, a retroviral vector expressing Oct4, or control retroviral empty vector, both plasmids contain puromycin resistance sequences) and pUMVC (encodes Gag-Pol) and pVSVG (encodes envelope protein of VSV). After 8 hours, the supernatants were replaced with fresh medium. Two days post transfection, supernatants of transfected cells were filtered, and Polybrene (hexadimethrine bromide; Sigma) was added to a final concentration of 8 μg/ml. These viral preparations were used to infect human adult kidney cells for 6 hours, after which fresh medium was added. This infection procedure was repeated on the next day. Three days post infection, the cells were selected for puromycin (puro) resistance at a concentration of 1.5 ug/ml. Cells were analyzed in the presence or absence of VPA treatment.

Creation of Renal Progenitor Gene OE Culture by Viral Infection. In order to create and optimize iRPCs, the present inventors propose to over-express developmental transcription factors specifying the embryonic renal progenitor pool ('renal progenitor genes') in human kidney cells via a viral system (e.g. lentivirus). The factors will be fluorescently tagged and/or associated with eukaryotic antibiotic resistance so as to enable isolation the desired cells. Three plasmids have been designed: Six2-IRES-GFP, Osr1-mCherry-Neomycin and mCherry-Pax2-Puro. These genes will be to over-expressed individually or in various combinations including in the presence or absence of the pluripotency/self-renewal gene Oct4. Infection will be carried out on primary human cortical renal cell cultures, mesenchymal stem cells and on the more defined RPTECs. Putative iRPCs generated from OE of single or multiple factors, will be then test in vitro in order to find the optimal genetic combination affording induction of progenitors from adult tissue.

Example 1

TSA/AzaC Treatment

The following experiments were performed in order to determine whether epigenetically repressed genes could be restored by treatment with a combination of the demethylating agent 5-aza-2'-deoxycytidine and the HDAC inhibitor TSA. Thus, human adult kidney cells were initially cultured in the presence or absence of TSA/AzaC for 24 hours. Changes in gene expression in at least three independent samples of human adult kidneys were analyzed after 24-h TSA/AzaC treatment by quantitative RT-PCR. In all cases a robust re-activation pattern was found including Six2 and Osr1 but not Sall1, Wt1 and Pax2 (FIGS. 1A-E). A wide-range of Six2 reinduction levels was noted (five-fold to 25-fold), probably due to primary culture heterogeneity.

Figure 1F:
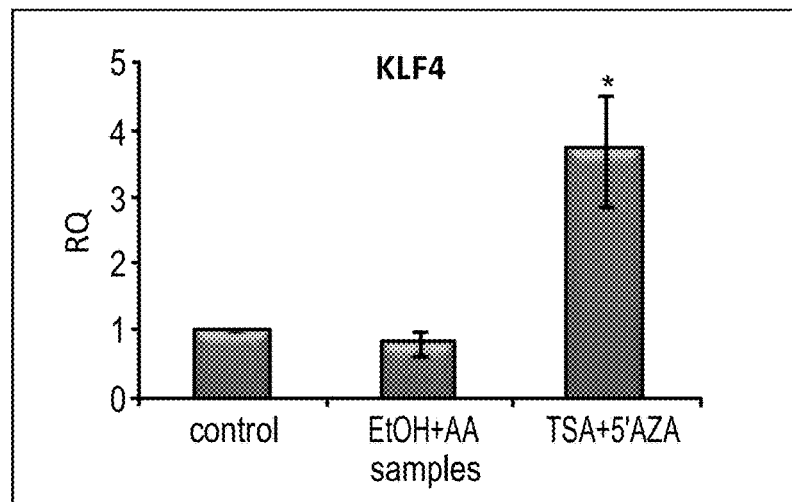
FIGS. 1A-T are bar graphs illustrating quantitative reverse transcription-polymerase chain reaction (qRT-PCR) analysis of human adult (A-J) and fetal (K-T) kidney cells subjected to TSA/AzaC (24 h). Shown are nephric-progenitor—(A-E and K-O), pluripotency/self renewal—(F-H and P-R) and mesenchymal-epithelial transition (MET, I-J and S-T) genes. At least three independent samples of human kidneys were used. Normalization was performed against GAPDH expression (endogenous control) and RQ (relative quantification) calculated relative to the untreated controls. Data were calculated as average±SD. *, $p<0.05$; **, $p<0.05$.
Figure 1G:
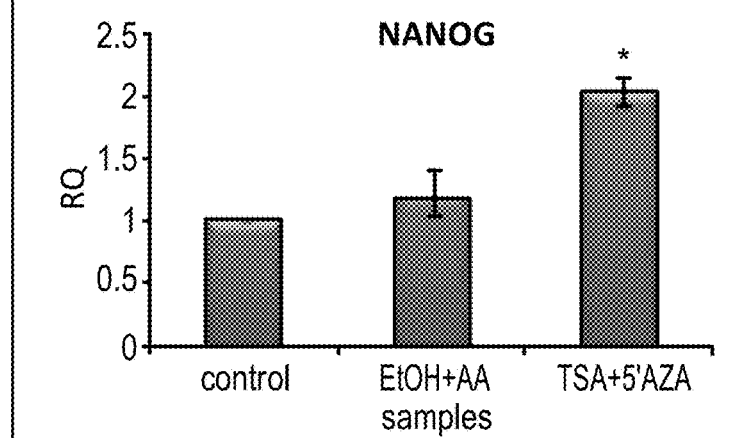
Figure 1H:
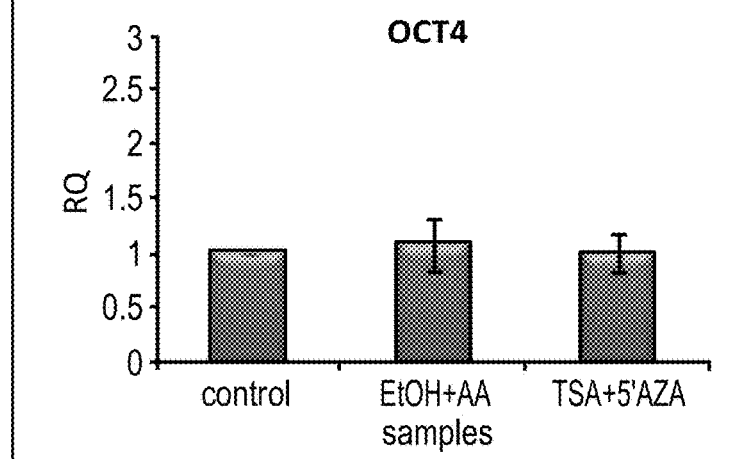
Figure 1N:
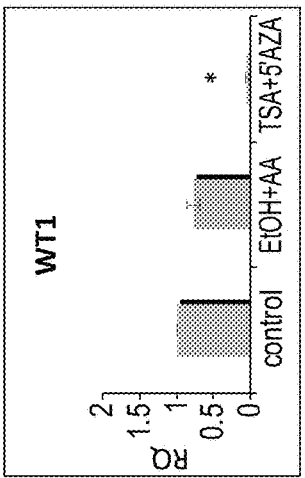
Figure 1O:
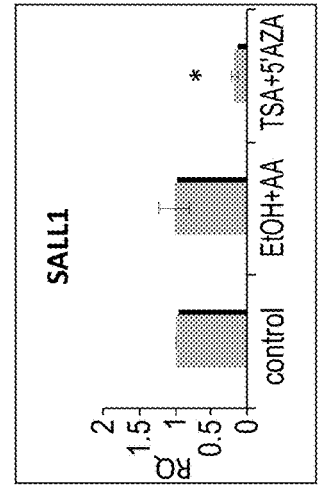
Figure 1K:
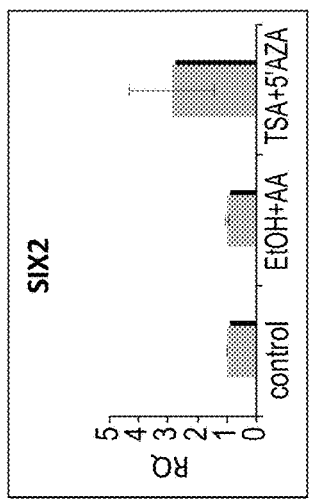
Figure 1L:
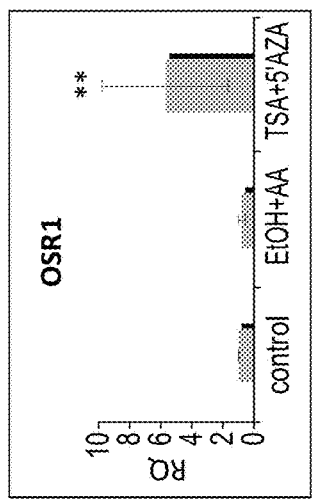
Figure 1M:
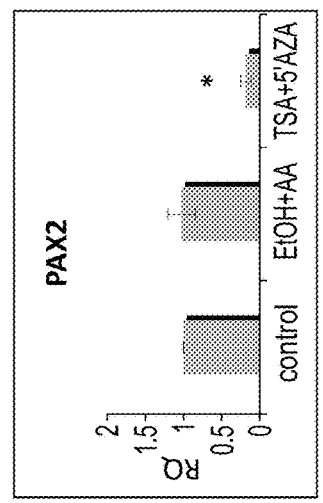
Figure 1I:
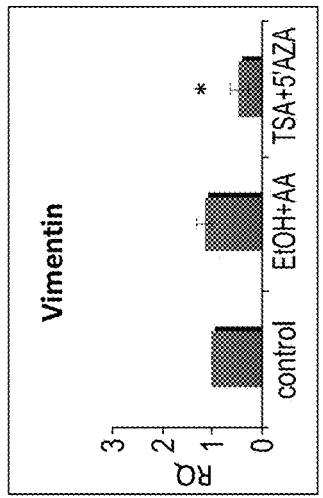
Figure 1J:
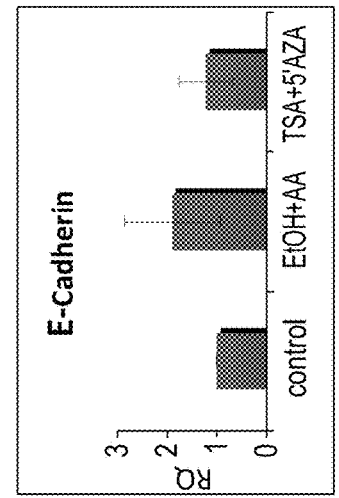
Figures 1P, 1Q, 1R:
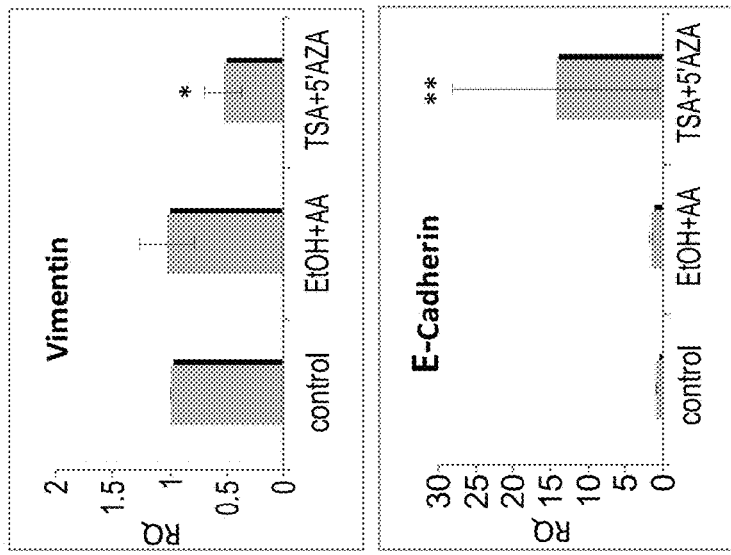
Figures 1S, 1T:
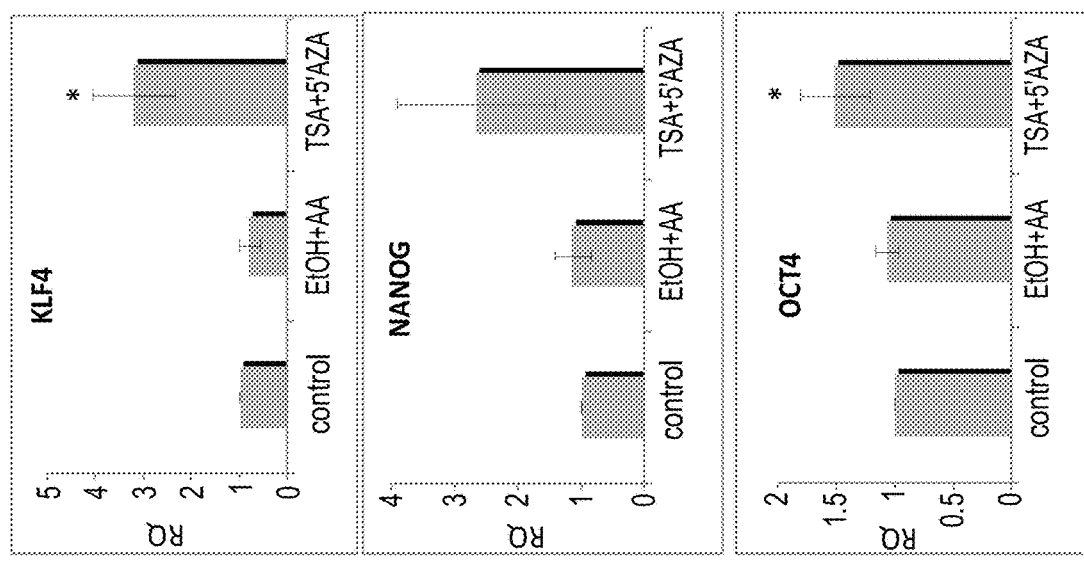

Several pluripotency/self-renewal genes, among which are Oct4, Nanog and Klf4, have been characterized to be crucial for somatic cell reprogramming. Therefore, the present inventors determined whether TSA/AzaC treatment brings about changes in their expression. Interestingly, expression of the ES cell transcription factors Nanog and Klf4 was significantly upregulated in human adult kidney cells, although Oct4 levels were unchanged (FIGS. 1F-H). Because kidney development progresses through mesenchymal to epithelial conversion of the MM (Vimentin$^+$) to epithelial progenitors (E-cadherin$^+$), the present inventors analyzed whether the reinduction of Six2 and Osr1 and pluripotency genes recapitulates early renal development and is associated with Vimentin upregulation. However, significant downregulation of Vimentin was found with no effect on E-cadherin levels (FIGS. 1I-J). Next, human fetal kidney cells derived from mid-gestation kidneys were evaluated. At this stage of nephrogenesis, there are opposing factors that govern the effects of treatment; on one hand the relative proportion of MM-progenitor cells is rather low compared to more differentiated epithelial cell types. In contrast, renal progenitor genes are still expected to be more abundantly expressed and less methylated at their promoters and thus less influenced. Altogether, a similar pattern of expression was found in treated human fetal kidney cells, upregulation of Six2 and Osr1 and reduction in Wt1, Pax2 and Sall1 levels (FIGS. 1K-O). In addition, induction of the pluripotency genes, Nanog and Klf4 was observed, similar to the adult kidney as well as of Oct4 (FIGS. 1P-R). Analysis of Vimentin/E-cadherin showed significant elevation of E-cadherin and reduction in Vimentin levels (FIGS. 1S-T).

Example 2

VPA Treatment

Figure 2C:
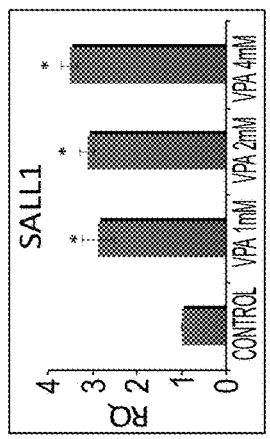
FIGS. 2A-T are bar graphs illustrating qRT-PCR analysis of human adult (A-J) and fetal (K-T) kidney cells subjected to VPA (24 h, three different concentrations). Shown are nephric-progenitor—(A-E and K-O), pluripotency/self renewal—(F-H and P-R) and mesenchymal-epithelial transition (MET, I-J and S-T) genes. At least three independent samples of human kidneys were used. Data were calculated as average±SD. *, $p<0.05$; **, $p<0.05$ after logarithmic transformation versus untreated controls.
Figure 2H:
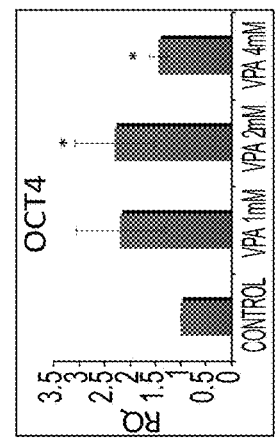
Figure 2B:
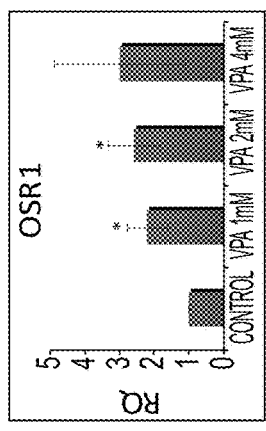
Figure 2E:
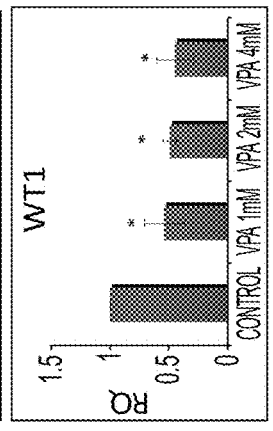
Figure 2G:
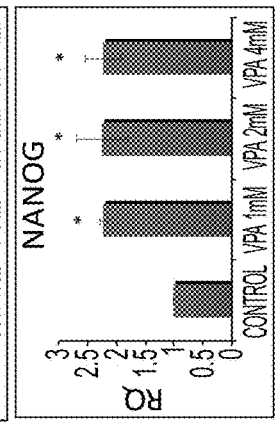
Figure 2J:
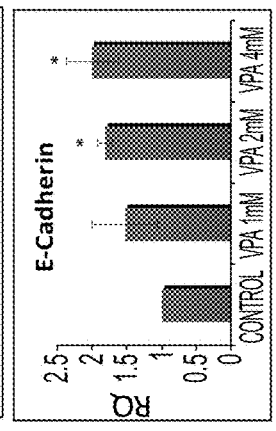
Figure 2A:
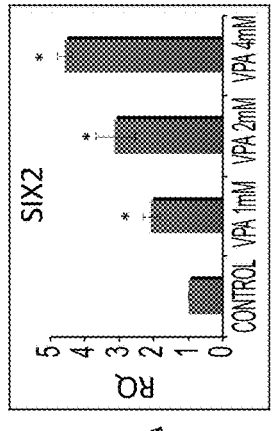
Figure 2D:
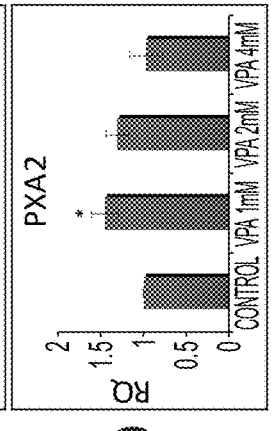
Figure 2F:
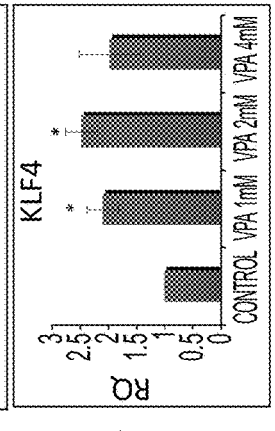
Figure 2I:
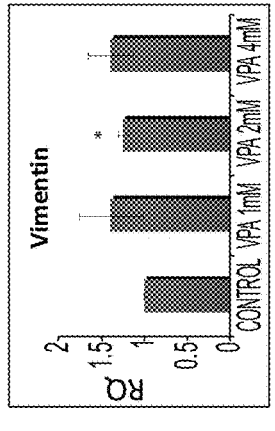

The following experiments were performed in order to determine the effects of VPA, an HDAC inhibitor on kidney cells. Changes in renal progenitor gene levels were assessed initially in adult human kidneys following a 24-hour VPA exposure. In contrast to TSA/AzaC, activation of Six2 was much similar among independent samples and a dose-dependent reinduction of Six2 could be observed in the presence of VPA (five-fold increase) (FIG. 2A). Furthermore, in addition to Six2, both Osr1 and Sall1 were found to be upregulated in a dose-dependent manner, while Pax2 levels were mildly elevated and Wt1 reduced (FIGS. 2A-E). Analysis of the pluripotency genes showed Nanog and Klf4 to be significantly up-regulated in all VPA concentrations, and Oct4 particularly in VPA-2 mM, while Vimentin/E-cadherin analysis demonstrated Vimentin levels to be mostly unchanged while E-cadherin mildly elevated (VPA-2 mM, 4 mM) (FIGS. 2F-J).

Almost exact findings were noted in human fetal kidney cells exposed to VPA; highest induction in Six2 levels (four-fold) and to a lesser extent of Osr1 and Sall1, with dose-dependent activation, concomitant with reduction of Wt1 and mild elevation in Pax2 levels (FIGS. 2K-O). Furthermore, levels of all pluripotency genes, Nanog, Klf4 and Oct4 (two-five fold increase at 4 mM VPA), and also E-cadherin were found to be significantly elevated along with the renal progenitor genes (FIGS. 2P-T).

Example 3

Changes in Protein Levels Following VPA Treatment

Having established that similar to TSA/AzaC, VPA treatment results in activation of specific renal progenitor genes as well as pluripotency genes, but also induces Sall1 and that these changes fluctuate less across human kidney samples, the present inventors analyzed changes at the protein level following exposure to 2 and 4 mM VPA. For western analysis the present inventors concentrated on Six2 protein as it was most substantially induced and it has a major role in specifying the renal stem cell population in the MM. Wt1, which is not induced at the gene level, was concomitantly analyzed. Western blots performed on both human fetal and adult kidney cells 24-h after VPA exposure clearly demonstrated an increment in Six2 protein levels in both types of cells (4 mM) and no changes in Wt1, both following their gene expression pattern (FIG. 3). Because certain surface markers characterize renal progenitor cells, FACS analysis of human adult and fetal kidney cells was performed so as to determine whether VPA exposure can also alter their expression levels. NCAM and its embryonic form, PSA-NCAM, both expressed on stem/progenitor cells of the condensed mesenchyme and on MM-derived progenitors showed significant upregulation in expression levels, with dramatic elevation (5-10-fold) in PSA-NCAM expression, especially in the adult kidney (FIGS. 4A-H). Surface markers such as CD133, that has been previously suggested to be expressed in adult renal stem cells and is widely distributed in either fetal and adult kidneys, showed milder changes (CD133) (FIGS. 4I-L).

Example 4

Six2 and Osr1 are Maintained Upon Tissue Culture Passage and Constant VPA Treatment Maintaining re-induction of Six2/Osr1 in cultured human kidney cells is potentially important if such cells were to be propagated in vitro for the purpose of cell therapy. The present inventors therefore determined whether Six2 and Osr1 are maintained upon tissue culture passage of adult cells. Two treatment protocols were employed; the first, 24-hour exposure to 4 mM VPA and the second constant exposure to VPA. It was found that while as expected gene levels were re-induced in the P0 cells following the transient VPA protocol with Six2 more profoundly so, in later passages they remained similar to controls. In contrast, constant VPA treatment resulted in significant Six2 and Osr1 re-induction upon culture passage and Six2 levels were even further up-regulated in P3 cells (FIG. 5AD). This was associated with an appearance of epithelial-like cell morphology compared with control cells and those transiently induced which acquired a fibroblastic morphology, in accordance with reports that human kidney cells may undergo transition into myofibroblasts (FIG. 5E-J).

Example 5

Epigenetic Modification of the Six2 Promoter

To test whether HDAC inhibition following VPA treatment functions in part through chromatin remodeling, ChIP was used to examine the post-transcriptionally modified state of the histones at the Six2 promoter. Recent evidence has indicated that unique patterns of histone modifications are responsible for transcriptional and lineage control. In particular, methylation of lysine 27 on histone subunit H3 (H3K27me) by the Polycomb complex is associated with transcriptional repression, whereas methylation of lysine 4 on H3 (H3K4me) is associated with gene activation. More generally, lysine acetylation of histones is also associated with transcriptional activation. Accordingly, multiple loci at the Six2 promoter region were examined for such changes by CHIP analysis. The promoter sites examined were designed at consecutive distance from the 5' transcription start site (TSS) (from ~90 bp upstream to ~1300 bp) (FIG. 6A). The Wt1 gene, which in contrast with Six2, was found to be modestly affected by VPA exposure was concomitantly analyzed. In addition to the chromatin state, DNA methylation profiles at the Six2 and Wt1 promoter regions were determined so as to detect epigenetic modifications at the DNA level. Treatment with VPA 4 mM significantly increased acetylated histones H4 in multiple Six2 promoter regions (upstream to the TSS: −92, −412, −541, −731, −955 and −1157) accompanied with significant increases in H3K4me but no change in H3K27me levels (FIGS. 6B-E). In contrast with Six2, a modest elevation in repressive H3K27me in the Wt1 promoter region was observed, but not H3K4me, likely to be responsible for little changes in gene expression (FIGS. 6B-E). In addition, MeDIP revealed DNA hypomethylation at the Six2 promoter loci regardless of VPA treatment, while methylation on Wt1 promoter was minimally effected by the treatment (FIG. 6F). Although the observed histone acetylation is directly modulated by HDAC inhibitor treatment, changes in methylation in both histones and DNA likely result from secondary effects. These results indicated that reactivation of Six2 is linked to epigenetic modification of histones at its promoter region leading to gene induction.

Example 6

Wnt Pathway Modulation Synergizes with VPA to Induce Six2/Osr1 Re-Induction

It has been suggested that in addition its major role as an HDAC inhibitor, VPA can inhibit GSK3β enabling the activation of the canonical Wnt pathway. Indeed, quantitative RT PCR analysis showed an elevation in β-catenin mRNA levels in VPA-treated human kidney cells (FIGS. 7A-B), and immunoflorescence disclosed cyoplasmic and nuclear accumulation of B-catenin compared to non-treated cells (FIGS. 7C-M). In addition, a strong up-regulation of Wnt4 mRNA was found (FIGS. 7A-B), which has been shown to drive differentiation in the MM progenitor population by opposing Six2 [7, 8](ref,). To evaluate the contribution of VPA-induced Wnt activation on renal progenitor gene expression, Wnt antagonists' sFRP1 and DKK1 were added to VPA and their effect was analyzed. When analyzing the sole effects of DKK1 and sFRP1 on Six2 expression in AK and FK cells, elevated Six2 levels in FK cells were observed, in which the Wnt pathway is likely to be more operative (FIGS. 7N-Q). sFRP1 had a synergistic effect on Six2 expression in both human adult and fetal kidney cells, while the synergistic effect of DKK1 was noted mostly in adult kidney cells. Both sFRP1 and DKK1 had a synergistic affect on Osr1 expression in both cells type; with little effect of the Wnt antagonists alone (FIGS. 7N-Q). While a comparison in Six2 levels between the various treatment groups of adult and fetal kidney cells showed, as expected, higher Six2 in FK cells, combined VPA/Wnt inhibitor treatment of AK cells resulted in Six2 re-induction to similar and even higher levels to those of control developing human kidney cells (FIG. 7R).

Example 7

Genetic Manipulation of HAK Cells

Having observed that epigenetic modulation of HAK cells results in re-activation of six2/osr1 but is not sufficient to induce epithelial to mesenchymal transition (EMT), but on the contrary preserves the epithelial phenotype, the present inventors began to analyze the additive effects of genetic manipulation on HAK cells. Since analyses demonstrated (see for example FIGS. 1G-H; 1Q-R) Nanog to be consistently up-regulated following epigenetic modification while Oct4 was less induced and even remained unchanged in HAK cells treated with VPA, the present inventors reasoned to test the contribution of overexpressing (OE) Oct4 via introduction of the human Oct4 gene into HAK cells in the presence or absence of epigenetic manipulation.

Human Oct4 gene was introduced into HAK cells by viral infection (FIGS. 8A-C) enabling over-expression of Oct4 simultaneously with VPA treatment. The cells were analyzed for renal 'stemness genes' and EMT. As illustrated in FIGS. 9A-F, over-expression of Oct4 re-induced the MM stem cell genes along with EMT.

Example 8

Phenotypic and Functional (Clonogenicity, Self-Renewal, Expansion and Multipotentiality) In Vitro Characterization of Putative iRPCs While reactivation of dormant renal-progenitor-genes and loss of segment-specific markers along with EMT phenotypic switch are important steps in induction of human renal progenitors, functional assays demonstrating stem/progenitor properties in vitro are crucial. Thus, following verification of the initial criteria of all putative human induced renal progenitor cells (iRPCs), they will be tested for clonogenicity, self renewal, expansion and multipotentiality. Single-cell clones raised will be phenotypically characterized by qRT-PCR, FACS and immunostaining (outlined above) for renal embryonic gene and surface marker expression, EMT and segment-specific markers. Additional methodologies are outlined herein below:

Clonogenicity/Self Renewal/Expansion. A single cell clonogenicity assay will be performed for human kidney derived cells as described in Pode-Shakked N. et al 2008. Briefly, cells at limiting dilution concentration are plated in matrigel (BD) coated 96-well micro well plates in of culture media and are further expanded. The number of colonized wells is recorded after 3-4 weeks.

Multipotentiality The potency of the induced renal progenitor cells (iRPCs) will be analyzed at the single cell level for the mesoderm lineage in general (fat, bone, smooth muscle, endothelium) as described by Dekel at al (JASN, 2006) and more specifically for renal segment-specification. If iRPCs are induced into 'true' MM-progenitors they may carry potential to differentiate into more than one nephron epithelial cell type. Wnt4 will be supplied as a well-known inductive signal for the differentiation of MM-progenitors, and single progenitors will be cultured with NIH3T3 cells stably expressing Wnt4. The protocol involves a 7 day induction period and which after the presence of types of epithelial cells that exist in glomeruli and renal tubules will be examined by immunostaining with EMT and segment-specific markers.

Example 9

Six2 and Osr1 are Maintained Upon Tissue Culture Passage of OE Oct4 Human Adult Kidney Cells Maintaining re-induction of Six2/Osr1 and the progenitor-state in cultured human kidney cells is highly important if such cells were to be propagated and expanded in vitro for the purpose of cell therapy. The present inventors therefore determined whether the morphologic switch accompanied by Six2 and Osr1 upregulation is maintained upon tissue culture passage of OE Oct4 HAK cells. It was found that OE Oct4 HAK cells can be continually propagated (P5, P7, P9) while showing a smaller round cell compared to spindle-shaped fibroblastic morphology in control AK and up-regulation of OSR1 and SIX2, indicative of maintaining a human renal progenitor state (FIGS. 10A-F and 11A-E).

REFERENCES

1. Metsuyanim, S., et al., *Accumulation of malignant renal stem cells is associated with epigenetic changes in normal renal progenitor genes*. Stem Cells, 2008. 26(7): p. 1808-17.
2. Boyle, S., et al., *Fate mapping using Cited1-CreERT2 mice demonstrates that the cap mesenchyme contains self-renewing progenitor cells and gives rise exclusively to nephronic epithelia*. Dev Biol, 2008. 313(1): p. 234-45.
3. Kobayashi, A., et al., *Six2 defines and regulates a multipotent self-renewing nephron progenitor population throughout mammalian kidney development*. Cell Stem Cell, 2008. 3(2): p. 169-81.
4. Self, M., et al., *Six2 is required for suppression of nephrogenesis and progenitor renewal in the developing kidney*. Embo J, 2006. 25(21): p. 5214-28.
5. Yamanaka, S., *Induction of pluripotent stem cells from mouse fibroblasts by four transcription factors*. Cell Prolif, 2008. 41 Suppl 1: p. 51-6.
6. Zhou, W. and C. R. Freed, *Adenoviral gene delivery can reprogram human fibroblasts to induced pluripotent stem cells*. Stem Cells, 2009. 27(11): p. 2667-74.
7. Kispert, A., S. Vainio, and A. P. McMahon, *Wnt-4 is a mesenchymal signal for epithelial transformation of metanephric mesenchyme in the developing kidney*. Development, 1998. 125(21): p. 4225-34.
8. Nishinakamura, R., *Stem cells in the embryonic kidney*. Kidney Int, 2008. 73(8): p. 913-7.

What is claimed is:

1. A method of reprogramming a differentiated adult epithelial renal cell to a cell having a progenitor phenotype, the method comprising transfecting the differentiated renal cell with a nucleic acid construct comprising a nucleic acid sequence encoding Oct4, thereby reprogramming the differentiated adult epithelial renal cell to a cell having a progenitor phenotype, and wherein said progenitor phenotype comprises Six2 and/or Osr1 expression and cell clonogenicity.

2. The method of claim 1, further comprising isolating the cell having the progenitor phenotype.

3. The method of claim 1, further comprising contacting the differentiated adult epithelial renal cell with at least one chromatin modifying agent.

4. The method of claim 1, wherein said differentiated adult epithelial renal cell is a human differentiated adult epithelial renal cell.

5. The method of claim 3, wherein said chromatin modifying agent is selected from the group consisting of valporic acid, 5-aza-2'-deoxycytidine and TSA.

6. A method of reprogramming a differentiated adult epithelial renal cell to a cell having a renal progenitor phenotype, the method comprising transfecting the differentiated adult epithelial renal cell with a nucleic acid construct comprising a nucleic acid sequence encoding at least one polypeptide which comprises Six2, thereby reprogramming the differentiated renal cell to a cell having a renal progenitor phenotype.

7. The method of claim 6, wherein said at least one polypeptide comprises Osr1 and Six2.

* * * * *

SEQUENCE LISTING

```
<160> NUMBER OF SEQ ID NOS: 41

<210> SEQ ID NO 1
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 1
ccaaggaaag ggagaacaac g                                                    21

<210> SEQ ID NO 2
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 2
gctggatgat gagtggtctg g                                                    21

<210> SEQ ID NO 3
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 3
gctgtcccac ttacagatgc a                                                    21

<210> SEQ ID NO 4
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 4
tcaaagcgcc agctggagtt t                                                    21

<210> SEQ ID NO 5
<211> LENGTH: 19
```

```
<212> TYPE: DNA
<213> ORGANISM: Artificial sequence
<220> FEATURE:
<223> OTHER INFORMATION: Single strand DNA oligonucleotide

<400> SEQUENCE: 5
cccagcgtct cttccatca                                              19

<210> SEQ ID NO 6
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 6
ggcgttgggt ggaaagg                                                17

<210> SEQ ID NO 7
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 7
tgtatggttt cagcgcgttg                                             20

<210> SEQ ID NO 8
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 8
gggttgaatg acatgaggga a                                           21

<210> SEQ ID NO 9
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 9
caatcttaag gtacacatgg gcac                                        24

<210> SEQ ID NO 10
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 10
tgcctcctag aaatgtcatg gg                                          22

<210> SEQ ID NO 11
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 11
```
agtgccaact ggaccattca                                                20

<210> SEQ ID NO 12
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 12
tctttgacca ccgctctcct                                                20

<210> SEQ ID NO 13
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 13
acaccctgca atctttcaga ca                                             22

<210> SEQ ID NO 14
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 14
gattccactt tgcgttcaag gt                                             22

<210> SEQ ID NO 15
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 15
gagaaccgag tgagaggcaa cc                                             22

<210> SEQ ID NO 16
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 16
catagtcgct gcttgatcgc ttg                                            23

<210> SEQ ID NO 17
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 17
aatacctcag cctccagcag atg                                            23

<210> SEQ ID NO 18
<211> LENGTH: 24
<212> TYPE: DNA
<213> ORGANISM: Artificial sequence

```
<220> FEATURE:
<223> OTHER INFORMATION: Single strand DNA oligonucleotide

<400> SEQUENCE: 18
tgcgtcacac cattgctatt cttc                                              24

<210> SEQ ID NO 19
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 19
accaggcact accgtaaaca ca                                                22

<210> SEQ ID NO 20
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 20
ggtccgacct ggaaaatgct                                                   20

<210> SEQ ID NO 21
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 21
aagcaaaaaa caggaccccc                                                   20

<210> SEQ ID NO 22
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 22
aacggaggca agattccca                                                    19

<210> SEQ ID NO 23
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 23
gaagccccac caccgtccta ga                                                22

<210> SEQ ID NO 24
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 24
acttaacccc acgggtccca ca                                                22
```

<210> SEQ ID NO 25
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 25
gaagtcgatt ctccggcgt                                          19

<210> SEQ ID NO 26
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 26
cccaccccca tcctagaaac                                         20

<210> SEQ ID NO 27
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 27
gggtagaatg tgcccggtga acaga                                   25

<210> SEQ ID NO 28
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 28
agggaaggcg gagaccgttt aagg                                    24

<210> SEQ ID NO 29
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 29
gctgcccaaa ctttcttccc ctg                                     23

<210> SEQ ID NO 30
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 30
cgaaaagggg tggatcgagg tg                                      22

<210> SEQ ID NO 31
<211> LENGTH: 19
<212> TYPE: DNA
<213> ORGANISM: Artificial sequence
<220> FEATURE:
<223> OTHER INFORMATION: Single strand DNA oligonucleotide

```
<400> SEQUENCE: 31
cgaggctcgg gttaccagt                                                    19

<210> SEQ ID NO 32
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 32
ccctgattgg tccggttatc t                                                 21

<210> SEQ ID NO 33
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 33
gcggcgctcg agaagttat                                                    19

<210> SEQ ID NO 34
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 34
ggtctcagaa ccgagtggga g                                                 21

<210> SEQ ID NO 35
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 35
tcgacagtca gccgcatct                                                    19

<210> SEQ ID NO 36
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 36
ctagcctccc gggtttctct                                                   20

<210> SEQ ID NO 37
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 37
tcgctctggt cttctacgtg g                                                 21

<210> SEQ ID NO 38
```

```
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 38
agtcttgagt gtgccaggcc                                           20

<210> SEQ ID NO 39
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 39
accaggcact accgtaaaca ca                                        22

<210> SEQ ID NO 40
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 40
tccaccaccc tgttgctgta                                           20

<210> SEQ ID NO 41
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 41
tccaccaccc tgttgctgta                                           20
```